(12) United States Patent (10) Patent No.: US 12,582,556 B2
Kawaura (45) Date of Patent: Mar. 24, 2026

(54) COMPRESSION DEVICE AND METHOD FOR ADHERING COMPRESSION DEVICE

(71) Applicant: TERUMO KABUSHIKI KAISHA, Tokyo (JP)

(72) Inventor: Masakatsu Kawaura, Campbell, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 476 days.

(21) Appl. No.: 17/935,700

(22) Filed: Sep. 27, 2022

(65) Prior Publication Data

US 2023/0015031 A1 Jan. 19, 2023

Related U.S. Application Data

(63) Continuation of application No. PCT/JP2021/009086, filed on Mar. 8, 2021.

(30) Foreign Application Priority Data

Mar. 27, 2020 (JP) ................................. 2020-059035

(51) Int. Cl.
| | |
|---|---|
| *A61F 13/00* | (2024.01) |
| *A61F 13/02* | (2024.01) |
| *A61F 13/0246* | (2024.01) |

(52) U.S. Cl.
CPC ........ *A61F 13/024* (2013.01); *A61F 13/0246* (2013.01); *A61F 2013/00412* (2013.01); *A61F 2013/00468* (2013.01)

(58) Field of Classification Search
CPC ................ A61F 13/024; A61F 13/0246; A61F 2013/00412; A61F 2013/00468;
(Continued)

(56) References Cited

U.S. PATENT DOCUMENTS

| | | | |
|---|---|---|---|
| 2009/0318952 A1 | 12/2009 | Bates et al. | |
| 2012/0116444 A1* | 5/2012 | Zodnik | ................ A61B 17/135 |
| | | | 606/202 |

(Continued)

FOREIGN PATENT DOCUMENTS

| | | |
|---|---|---|
| CN | 105559792 A | 5/2016 |
| CN | 209332163 U | 9/2019 |

(Continued)

OTHER PUBLICATIONS

International Search Report (PCT/ISA/210) with English translation and Written Opinion (PCT/ISA/237) mailed on Apr. 27, 2021, by the Japanese Patent Office as the International Searching Authority for International Application No. PCT/JP2021/009086.

(Continued)

*Primary Examiner* — Tan-Uyen T Ho
*Assistant Examiner* — Bridget E. Rabaglia
(74) *Attorney, Agent, or Firm* — BUCHANAN INGERSOL & ROONEY PC

(57) ABSTRACT

A compression device includes: an adhesive sheet having an adhesion surface; and a compression member configured to compress a biological surface. The compression member includes: a pressing body configured to press the biological surface by extending in a thickness direction of the adhesive sheet; and a holding body fixed to the adhesive sheet and configured to hold the pressing body. In a plan view seen in the thickness direction, a receiving portion, which is a region in which the adhesive sheet is not disposed or a region defined by a concave portion in an outer edge of the adhesive sheet and which is configured to receive a medical insertion member, is provided outside an outer edge of the holding body. The holding body includes, at a position adjacent the receiving portion, an identification portion configured to be (Continued)

visually identified in the plan view seen in the thickness direction.

20 Claims, 19 Drawing Sheets

(58) Field of Classification Search
CPC ............ A61F 13/00; A61F 2013/00361; A61F 2013/00365; A61F 2013/0041; A61F 2013/00174; A61F 13/02; A61F 5/34; A61F 13/05; A61F 13/01021; A61B 2017/00907; A61B 2017/00924; A61B 2090/3937; A61B 17/1325; A61B 17/135; A61B 2017/12004; A61B 17/0057; A61B 17/12; A61B 2017/00557; A61B 2017/00951; A61B 2090/0807; A61B 2017/00659; A61B 17/085; A61B 17/1322; A61B 17/12009; A61B 17/132; A61B 17/3403; A61B 2017/00442; A61M 2025/0273; A61M 25/02; A61M 2025/0253; A61M 2025/0246; A61M 27/00; A61M 5/158; B32B 2535/00
See application file for complete search history.

(56) References Cited

U.S. PATENT DOCUMENTS

| | | | |
|---|---|---|---|
| 2016/0120450 A1 | 5/2016 | Sakurai | |
| 2019/0029693 A1* | 1/2019 | Okamura | ............. A61B 17/135 |
| 2019/0133602 A1 | 5/2019 | Kiemeneij et al. | |
| 2019/0314035 A1 | 10/2019 | Hopkinson et al. | |
| 2021/0186521 A1 | 6/2021 | Kawaura et al. | |

FOREIGN PATENT DOCUMENTS

| | | |
|---|---|---|
| CN | 110461255 A | 11/2019 |
| JP | 2005521464 A | 7/2005 |
| JP | 3136037 U | 9/2007 |
| JP | 2020-022679 A | 2/2020 |
| KR | 10-2011-0088115 A | 8/2011 |
| WO | 2018181314 A1 | 10/2018 |
| WO | 2020017653 A1 | 1/2020 |
| WO | 2020/050420 A1 | 3/2020 |

OTHER PUBLICATIONS

The extended European Search Report issued Jul. 27, 2023, by the European Patent Office in corresponding European Patent Application No. 21775389.6-1122. (117 pages).
Office Action/Search Report (The First Office Action) issued on May 29, 2025, in corresponding Chinese Patent Application No. 202180007685.0 and machine English translation of the Office Action/Search Report. (14 pages).

* cited by examiner

FIG. 7

START

↓

| ADHERING STEP | ⟋ S1 |

↓

| FIRST COMPRESSION STEP | ⟋ S2 |

↓

| REMOVING STEP | ⟋ S3 |

↓

| SECOND COMPRESSION STEP | ⟋ S4 |

↓

END

COMPRESSION DEVICE AND METHOD FOR ADHERING COMPRESSION DEVICE

CROSS-REFERENCES TO RELATED APPLICATIONS

This application is a continuation of International Patent Application No. PCT/JP2021/009086 filed on Mar. 8, 2021, which claims priority to Japanese Patent Application No. 2020-059035 filed on Mar. 27, 2020, the entire content of both of which is incorporated herein by reference.

TECHNOLOGICAL FIELD

This disclosure generally relates to a compression device, a method for adhering a compression device and a compression method.

BACKGROUND DISCUSSION

In recent years, various forms of examinations and treatments using catheters have been performed in medical institutions. A catheter is percutaneously inserted into a blood vessel from a puncture site formed at a wrist, an inguinal region, and the like, and is carried through the blood vessel to a site to be examined or treated, for example. After an examination or treatment by a health care worker is completed, an elongated insertion member such as a puncture needle, a catheter, and a sheath used for introducing a catheter into a living body is removed from the puncture site, and the puncture site is stopped from bleeding.

Japanese Patent Application Publication No. 2005-521464 (JP-T-20050521464) discloses a dressing as a compression device that applies compression to a wound of a patient after removing a sheath. The dressing in this Japanese patent application publication includes an inflatable bladder having a deflated state in which a membrane is adjacent to an end wall and an inflated state in which the membrane is spaced from the end wall. In addition, the dressing includes a holding portion that holds the bladder against a skin of the patient at a position at which the wound is substantially covered. In Japanese Patent Application Publication No. 2005-521464, the holding portion includes a flexible web that is connected to the end wall of the bladder and that protrudes outward from the end wall of the bladder, and one surface of the flexible web is provided with an adhesive layer that adheres to the skin of the patient.

SUMMARY

In the dressing as the compression device described in Japanese Patent Application Publication No. 2005-521464, the adhesive layer provided on the one surface of the flexible web is adhered to the skin of the patient that is a biological surface, and the bladder is brought into the inflated state, so that the wound of the patient can be compressed by the bladder.

However, in the dressing described in the Japanese patent application publication, there is still room for improvement in efficiency of aligning the bladder to a predetermined compression position on the biological surface.

Disclosed here is a compression device that can be easily positioned at an appropriate position on a biological surface and a method for adhering a compression device.

A compression device according to a first aspect includes: an adhesive sheet having an adhesion surface configured to be adhered to a biological surface, wherein the adhesive sheet possessing a thickness that extends in a thickness direction of the adhesive sheet; and a compression member that is fixed to the adhesive sheet and that is configured to compress the biological surface. The compression member includes a pressing body configured to press the biological surface by extending in the thickness direction of the adhesive sheet, and a holding body that is fixed to the adhesive sheet on a side opposite to the adhesion surface and that holds the pressing body so that the pressing body is extendable in the thickness direction, the holding body including an outer edge. A receiving portion is configured to receive a medical insertion member, and the receiving portion is provided outside the outer edge of the holding body as seen in a plan view in the thickness direction. The receiving portion is a region in which the adhesive sheet is not disposed or a region defined by a concave portion in an outer edge of the adhesive sheet. The holding body includes, at a position adjacent to the receiving portion, an identification portion configured to be visually identified in the plan view seen in the thickness direction.

According to one embodiment of this disclosure, the pressing body includes an inflatable portion that is to be disposed between the biological surface and the holding body in a state in which the adhesion surface of the adhesive sheet is adhered to the biological surface and that is inflatable in the thickness direction by supplying a fluid, and at least a part of the identification portion is provided at a position overlapping with the inflatable portion of the pressing body in the plan view seen in the thickness direction.

According to one embodiment of this disclosure, the identification portion includes a region marker that enables visual identification of a predetermined region in the plan view seen in the thickness direction.

According to one embodiment of this disclosure, the region marker is a frame line marker that surrounds a portion having translucency in the thickness direction.

According to one embodiment of this disclosure, the holding body includes a portion having translucency in the thickness direction in an adjacent periphery outside the region marker in the plan view seen in the thickness direction.

According to one embodiment of this disclosure, the identification portion includes, within the predetermined region identified by the region marker, a position marker that is visually identified in the plan view seen in the thickness direction and that indicates a predetermined reference position.

According to one embodiment of this disclosure, the position marker is a line segment marker that is curved and extends in an arc shape in the plan view seen in the thickness direction.

In a method for adhering a compression device on a biological surface according to a second aspect of this disclosure, the compression device includes: an adhesive sheet having an adhesion surface configured to be adhered to the biological surface, with the adhesive sheet possessing a thickness that extends in a thickness direction of the adhesive sheet; and a compression member that is fixed to the adhesive sheet and that is configured to compress the biological surface. The compression member includes: a pressing body configured to press the biological surface by extending in the thickness direction of the adhesive sheet; and a holding body that is fixed to the adhesive sheet on a side opposite to the adhesion surface and that holds the pressing body so that the pressing body is extendable in the thickness direction, the holding body including an outer edge. A receiving portion configured to receive a medical insertion member is provided outside the outer edge of the holding body as seen in a plan view in the thickness direction, with the receiving portion being a region in which the adhesive sheet is not disposed or a region defined by a concave portion in an outer edge of the adhesive sheet. The holding body includes, at a position adjacent to the receiving portion, an identification portion configured to be visually identified in the plan view seen in the thickness direction. The method comprises adhering the adhesive sheet to the biological surface while the medical insertion member extends into a living body from the biological surface, with a portion of the medical insertion member being exposed to outside the biological surface. The adhering of the adhesive sheet to the biological surface including adhering the adhesive sheet to the biological surface so that the portion of the medical insertion member that is exposed to outside the biological surface is received in the receiving portion, and the adhering of the adhesive sheet to the biological surface including adhering the adhesive sheet to the biological surface while an insertion portion of the medical insertion member, which is located on a surface that is the same as the biological surface, is aligned with the identification portion.

According to one embodiment of this disclosure, the identification portion includes a region marker that enables visual identification of a predetermined region in the plan view seen in the thickness direction, and the adhesive sheet is adhered to the biological surface in the state in which the portion of the medical insertion member inserted into the living body from the biological surface, the portion being exposed to the outside from the biological surface, is received by the receiving portion, and in a state in which the whole insertion portion of the medical insertion member, which is located on the same surface as the biological surface, is aligned within the region marker.

According to one embodiment of this disclosure, the identification portion includes, within the predetermined region identified by the region marker, a position marker that is visually identified in the plan view seen in the thickness direction and that indicates a predetermined reference position, and the adhesive sheet is adhered to the biological surface in the state in which the portion of the medical insertion member inserted into the living body from the biological surface, the portion being exposed to the outside from the biological surface, is received by the receiving portion, in a state in which the whole insertion portion of the medical insertion member, which is located on the same surface as the biological surface, is aligned within the region marker, and in a state in which a part of the insertion portion is aligned with the position marker.

Another aspect disclosed here involves a compression device to be adhered to a biological surface of a living body to apply compression to a puncture site penetrating the biological surface of the living body. The compression device comprises an adhesive sheet, a holding body and a pressing body. The adhesive includes an adhesion surface configured to face towards and be adhered to the biological surface, with the adhesion surface being a lower surface of the adhesive sheet and the adhesive sheet also including an upper surface spaced from the lower surface of the adhesive sheet in a thickness direction of the adhesive sheet. The adhesive surface is configured to surround an open central area of the adhesive sheet as seen in a plan view of the compression device, with the open central area of the adhesive sheet extending in the thickness direction of the adhesive sheet so that the open central area of the adhesive sheet is open at both the upper and lower surfaces of the adhesive sheet, the adhesive sheet possessing an outer periphery. The holding body is fixed to the upper surface of the adhesive sheet and spans across the open central area of the adhesive sheet. The pressing body is mounted on the holding body so that the pressing body is held by the holding body at a position in the open central area of the adhesive sheet. The pressing body is configured to expand in the thickness direction to apply the compression to the puncture site penetrating the biological surface of the living body when the adhesive sheet is adhered to the biological surface. The adhesive sheet includes a receiving portion constituted by a cut-out portion of the adhesive sheet that is cut-out from the outer periphery of the adhesive sheet toward the open central area of the adhesive sheet, and the receiving portion is located radially outwardly of the outer edge of the holding body as seen in the plan view of the compression device and is configured to receive an elongated medical insertion member located in the puncture site penetrating the biological surface of the living body. The holding body including an identification portion that is visually identifiable in the plan view and that identifies a location for positioning the compression device relative to the elongated medical insertion member when the compression device is adhered to the biological surface of the living body, with the identification portion being located adjacent to and inwardly of the receiving portion as seen in the plan view of the compression device.

According to this disclosure, the compression device that can be easily positioned at an appropriate position on the biological surface and the method for adhering the compression device can be provided.

BRIEF DESCRIPTION OF THE DRAWINGS

FIG. 7 is a flowchart showing an example of a method for compressing a biological surface using the compression device shown in FIG. 1, the method including a method for adhering a compression device, according to the first embodiment of this disclosure.

DETAILED DESCRIPTION

Figure 1:
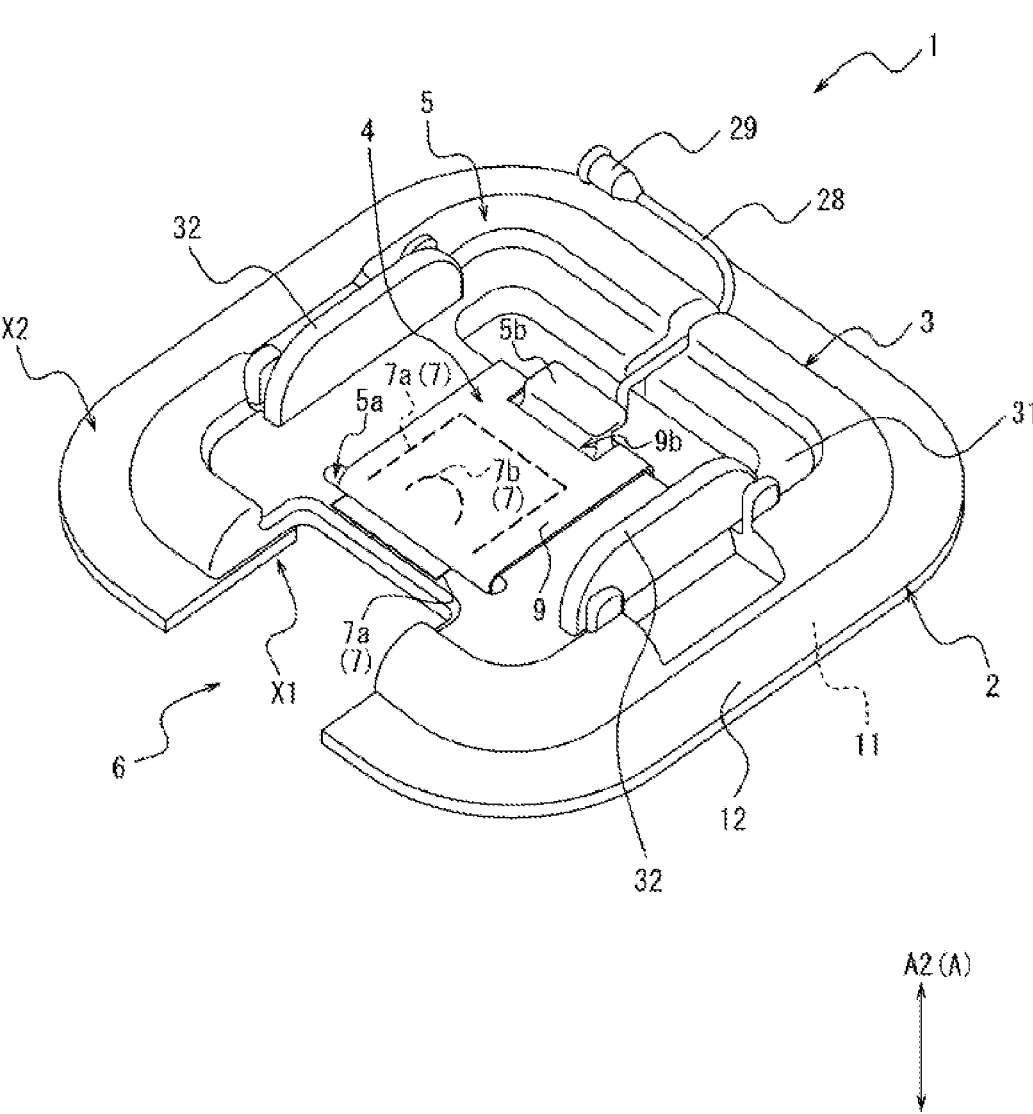
FIG. 1 is a perspective view of a compression device according to a first embodiment of this disclosure as seen from an upper surface side.

Set forth below with reference to the accompanying drawings is a detailed description of embodiments of a compression device, adhering method and compression method representing examples of the new compression device and methods disclosed here. In the drawings, common members and portions are denoted by the same reference numerals.

First Embodiment

Figure 2:
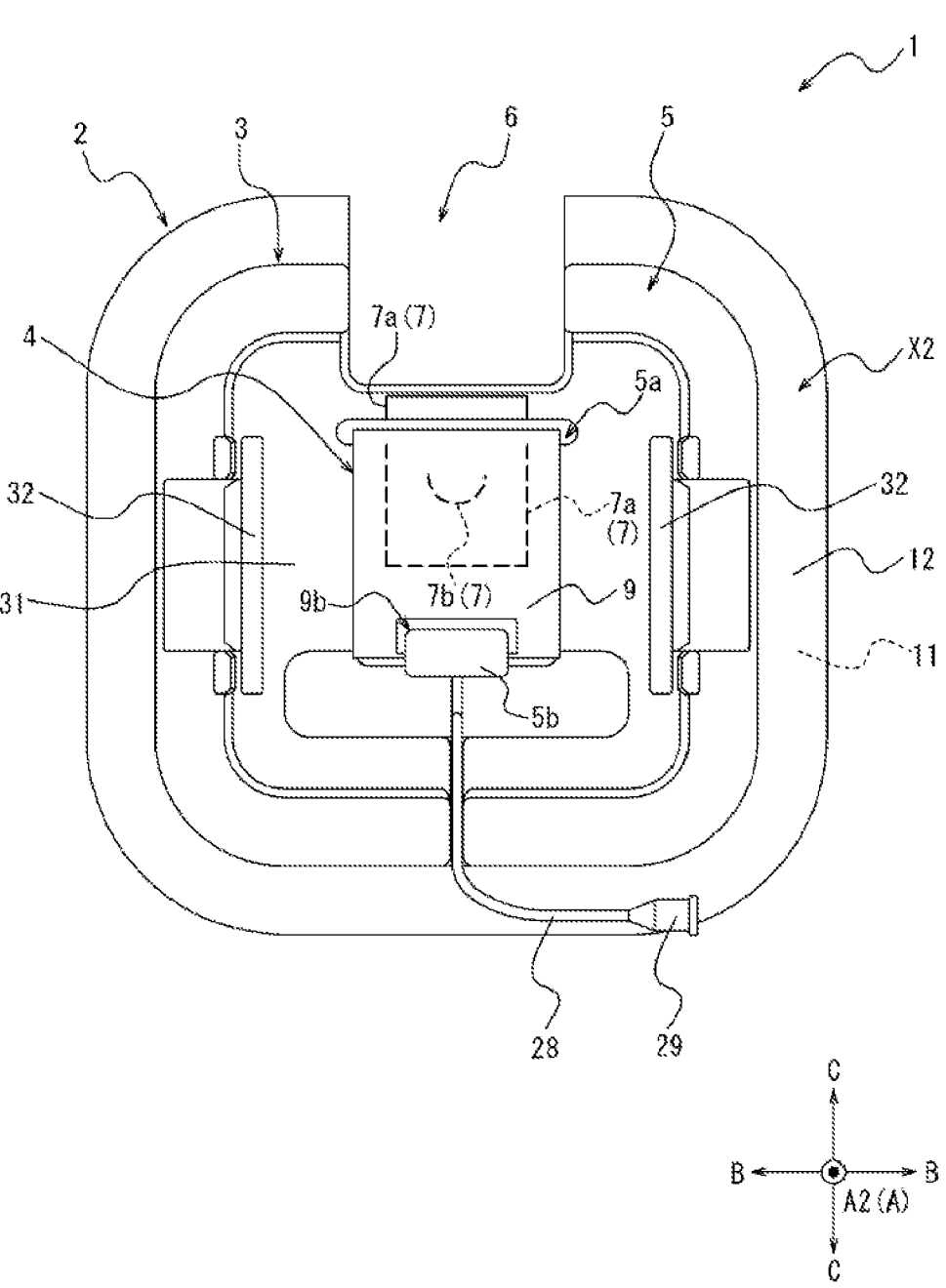
FIG. 2 is a top view of the compression device shown in FIG. 1.
Figure 3:
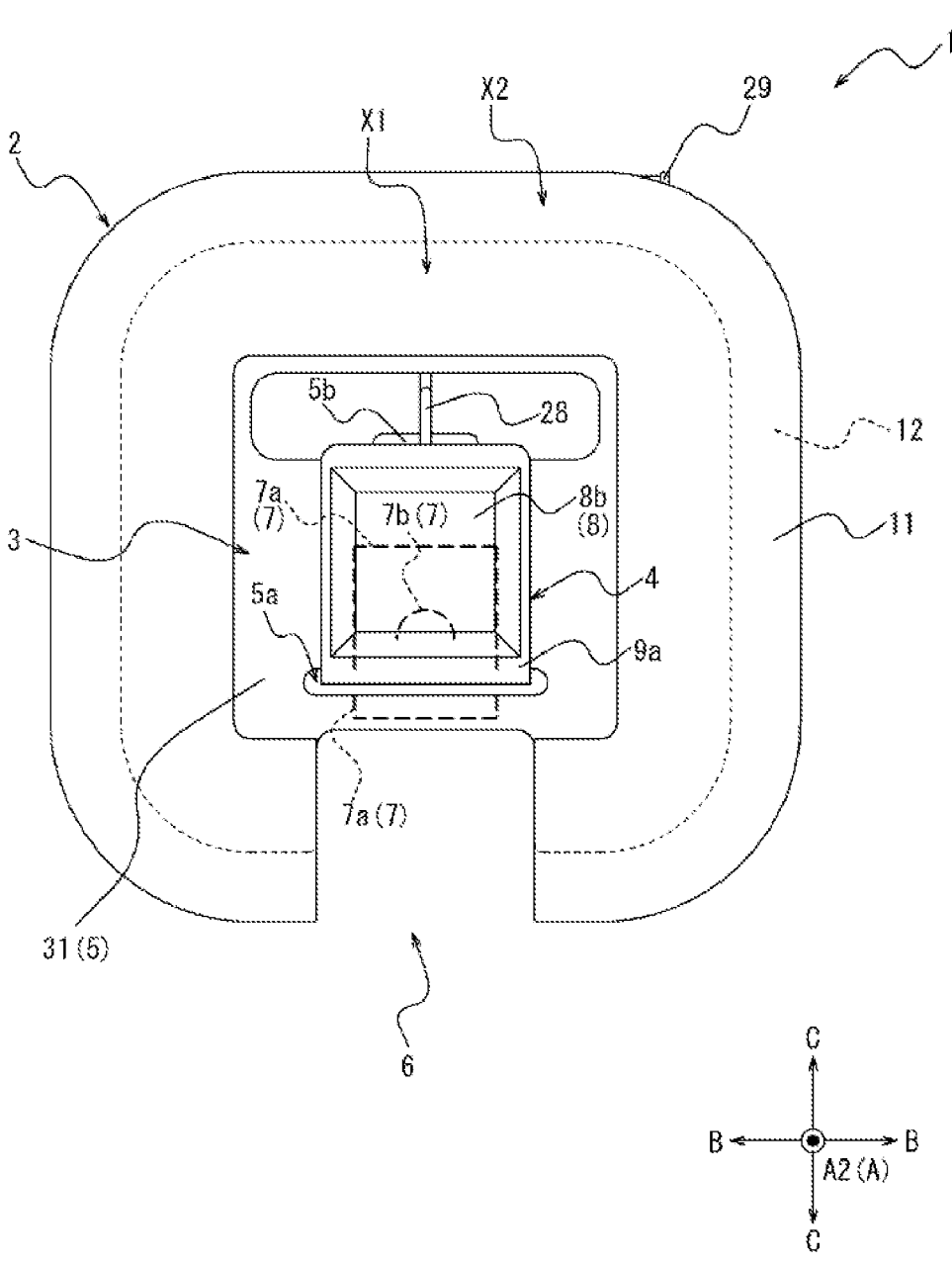
FIG. 3 is a bottom view of the compression device shown in FIG. 1.
Figure 4:
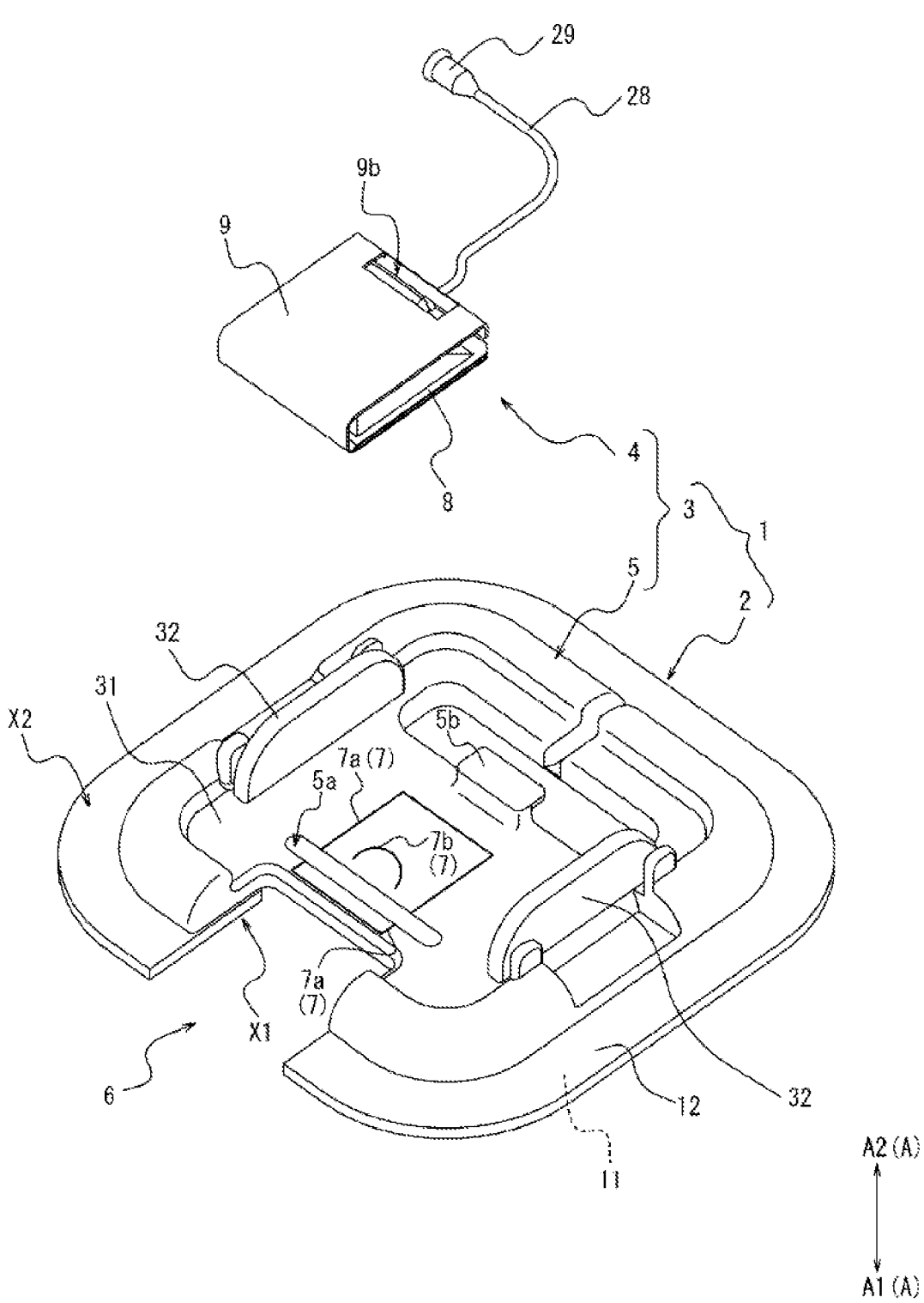
FIG. 4 is an exploded perspective view of the compression device shown in FIG. 1.
Figure 5:
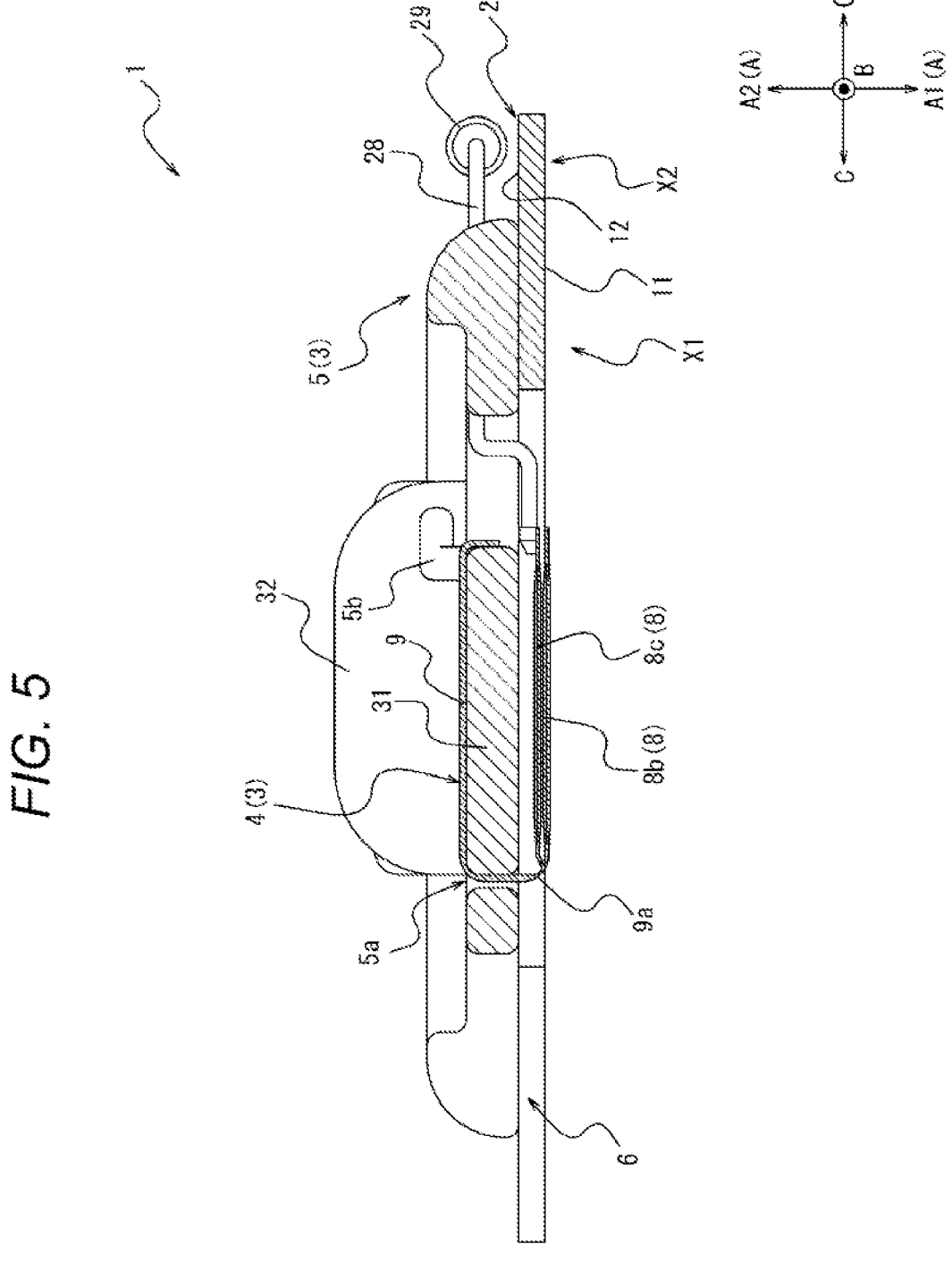
FIG. 5 is a section view of the compression device shown in FIG. 1 in a state in which an inflatable portion is in a deflated form.
Figure 6:
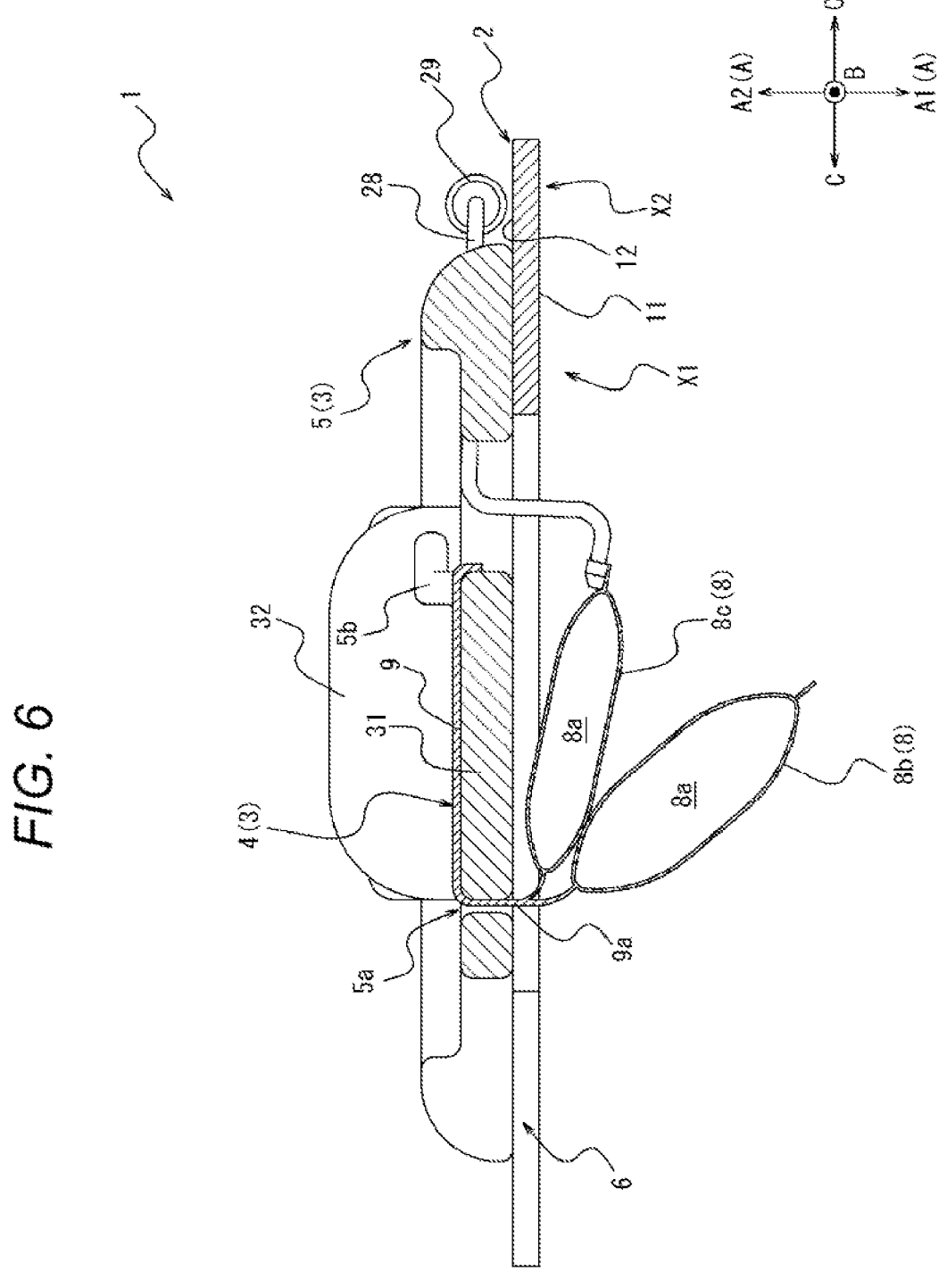
FIG. 6 is a section view of the compression device shown in FIG. 1 in a state in which the inflatable portion is in an inflated form.

FIGS. 1 to 6 are views showing a compression device 1 according to an embodiment of this disclosure. Specifically, FIG. 1 is a perspective view of the compression device 1 as seen from an upper surface side. FIGS. 2 and 3 are plan views of the compression device 1. Specifically, FIG. 2 is a top view of the compression device 1. FIG. 3 is a bottom view of the compression device 1. FIG. 4 is an exploded perspective view of the compression device 1. FIGS. 5 and 6 are section views of the compression device 1 in the same cross section. Details will be described later, and FIGS. 5 and 6 show different states of the compression device 1.

The compression device 1 includes an adhesive sheet 2 and a compression member 3.

The adhesive sheet 2 has an adhesion surface 11, which is capable of being adhered to a biological surface, on one side in a thickness direction A. The compression member 3 is attached to the adhesive sheet 2. Specifically, the compression member 3 is fixed to the adhesive sheet 2 on a side opposite to the adhesion surface 11. The compression member 3 can compress the biological surface in a state in which the adhesion surface 11 is adhered to the biological surface. Accordingly, the compression device 1 is fixed to a position on the biological surface by adhering the adhesion surface 11 on the biological surface. According to the compression device 1, a predetermined site on the biological surface can be compressed by the compression member 3 in a state in which the adhesion surface 11 of the adhesive sheet 2 is adhered to the biological surface. The predetermined site on the biological surface includes, for example, a wound on the biological surface or its vicinity formed by inserting a medical insertion member such as a puncture needle, a catheter, and a sheath into a blood vessel of a living body. After the above-mentioned medical insertion member is removed from the living body, bleeding can be stopped by compressing the wound on the biological surface or its vicinity by the compression member 3 for a predetermined time.

More specifically, the compression member 3 includes a pressing body 4 and a holding body 5. The pressing body 4 can press the biological surface by extending in the thickness direction A of the adhesive sheet 2. The holding body 5 is fixed to the adhesive sheet 2 on the side opposite to the adhesion surface 11, and holds the pressing body 4 so that the pressing body 4 is extendable in the thickness direction A. As generally shown in FIGS. 1 and 4, the adhesive sheet 2 surrounds an open central region (i.e., the central part of the adhesive sheet is open), and the holding body 5 together with the pressing body 4 spans this open central region of the adhesive sheet 2.

In a plan view of the compression device 1 seen in the thickness direction A (see FIGS. 2 and 3), a receiving portion 6, which is a region in which the adhesive sheet 2 is not disposed and which is capable of receiving a medical insertion member 100 to be described later (see FIGS. 8A-8E or the like), is provided outside an outer edge of the holding body 5. More specifically, the adhesive sheet 2 according to the present embodiment includes a first portion X1 that overlaps with the holding body 5 and a second portion X2 that does not overlap with the holding body 5 in the plan view of the compression device 1 seen in the thickness direction A (see FIGS. 2 and 3). As shown in FIG. 2, in a top view of the compression device 1, most of an outer periphery of the outer edge of the holding body 5 according to the present embodiment is surrounded by the second portion X2 of the adhesive sheet 2. In other words, the outer edge of the holding body 5 of the compression device 1 according to the present embodiment includes only a small part on the outside thereof at which the second portion X2 of the adhesive sheet 2 is not disposed. The receiving portion 6 according to the present embodiment is a region around the holding body 5 in which the second portion X2 of the adhesive sheet 2 is not disposed.

The receiving portion 6 according to the present embodiment is a region in which the adhesive sheet 2 is not disposed outside the outer edge of the holding body 5 in the plan view of the compression device 1 seen in the thickness direction A (see FIGS. 2 and 3), but is not limited to the configuration. The receiving portion 6 may be a region defined by a concave portion in an outer edge of the adhesive sheet 2. For example, in the plan view of the compression device 1 seen in the thickness direction A (see FIGS. 2 and 3), the concave portion recessed from the periphery of the adhesive sheet 2 may be formed in a part of the outer edge of the adhesive sheet 2 outside the outer edge of the holding body 5 (a cut-out portion of the adhesive sheet extending from the outer periphery of the adhesive sheet towards the open central region). In such a case, the receiving portion 6 may be a region defined by the concave portion (i.e., the receiving portion 6 may be a region defined by the cut-out or gap in the annular-shaped adhesive sheet 2). That is, the receiving portion 6 may be formed in a region in which the adhesive sheet 2 is disposed outside the outer edge of the holding body 5 in the plan view of the compression device 1 seen in the thickness direction A (see FIGS. 2 and 3). In other words, a position in which the receiving portion 6 is formed is not limited to the region in which the adhesive sheet 2 is not disposed outside the outer edge of the holding body 5 in the plan view of the compression device 1 seen in the thickness direction A (see FIGS. 2 and 3).

By providing the receiving portion 6, the compression device 1 can be attached to the biological surface in a state in which a portion of the medical insertion member 100 (see FIG. 8A or the like) extending outside the living body passes through the receiving portion 6. Accordingly, the compression device 1 can be easily attached to a desired position on the biological surface even when there is the portion of the medical insertion member 100 (see FIG. 8A or the like) extending outside the living body.

Here, the holding body 5 of the compression member 3 includes an identification portion 7 at a position adjacent to the receiving portion 6. A configuration of the identification portion 7 is not particularly limited as long as the identification portion 7 can be visually identified in the plan view seen in the thickness direction A. The identification portion 7 may be, for example, one convex portion protruding from an upper surface of the holding body 5 or a concave-convex portion formed by a set of a plurality of convex portions. The identification portion 7 may be, for example, a concave portion such as a groove portion formed on the upper surface of the holding body 5. In addition, the identification portion 7 may be, for example, one convex portion protruding from a lower surface of a portion having translucency of the holding body 5 or a concave-convex portion formed by a set of a plurality of convex portions. The portion having translucency in the thickness direction A means a semi-transparent or transparent portion in the thickness direction A. The identification portion 7 may be, for example, a concave portion such as a groove portion formed on the lower surface of the portion having translucency of the holding body 5. Further, for example, the identification portion 7 may have a transmittance different from that of the periphery. As an example, the identification portion 7 may be a portion having a transmittance lower than that of the periphery, which is located in the portion having translucency of the holding body 5. In addition, for example, the identification portion 7 may have a color different from that of the periphery. The identification portion 7 may be, for example, a paint or the like with which a part of the upper surface or the lower surface of the holding body 5 is coated. As described above, the configuration of the identification portion 7 is not particularly limited as long as the identification portion 7 can be identified separately (visually distinguishable) from the periphery in a plan view under a usage environment, particularly a top view (see FIG. 2).

The identification portion 7 according to the present embodiment is adjacent to the receiving portion 6 on a side on which an inflatable portion 8, which will be described later, of the pressing body 4 is located in the plan view of the compression device 1 seen in the thickness direction A. In addition, according to the present embodiment, in the plan view of the compression device 1 seen in the thickness direction A, a maximum width of the identification portion 7 is smaller than a maximum width of the inflatable portion 8, which will be described later, of the pressing body 4. The maximum width of the identification portion 7 according to the present embodiment means a maximum width of a region marker 7*a* to be described later in a width direction B as shown in FIG. 2. In addition, the maximum width of the inflatable portion 8 according to the present embodiment means a maximum width of the inflatable portion 8 in the width direction B as shown in FIG. 2. The width direction B means a direction orthogonal to an arrangement direction C in which the receiving portion 6 and the inflatable portion 8 of the pressing body 4 are arranged in the plan view of the compression device 1 seen in the thickness direction A.

According to the present embodiment, in the plan view of the compression device 1 seen in the thickness direction A, the maximum width of the identification portion 7 is smaller than a minimum width of the receiving portion 6. The minimum width of the receiving portion 6 means a minimum width of the receiving portion 6 in the width direction B as shown in FIG. 2.

The details will be described later, and the identification portion 7 according to the present embodiment includes both the region marker 7*a* and a position marker 7*b*. The region marker 7*a* means a marker that enables visual identification of a predetermined region (the region marker 7*a* is visually identifiable or visually distinguishable as seen by way of example in FIGS. 1-4) in the plan view seen in the thickness direction A. The region marker 7*a* according to the present embodiment represents a region in which the compression member 3 can compress the biological tissue with a compression force of a first predetermined value or more in a state in which the compression device 1 is attached to the biological surface. In addition, the position marker 7*b* is a marker that can be visually identified (the position marker 7*b* is visually identifiable or visually distinguishable as seen by way of example in FIGS. 1-4) in the plan view seen in the thickness direction A within the predetermined region that can be identified by the region marker 7*a*. In addition, the position marker 7*b* indicates a predetermined reference position within the predetermined region that can be identified by the region marker 7*a*. The position marker 7*b* according to the present embodiment indicates a reference position for aligning a part of an outer surface of an insertion portion 100*a* (see FIG. 8A) of the medical insertion member 100 (see FIG. 8A), which is located on the same surface as the biological surface. More specifically, the position marker 7*b* according to the present embodiment indicates a reference position for aligning the medical insertion member 100 (see FIG. 8A) requiring a particularly large compression force in the predetermined region that can be identified by the region marker 7*a*. That is, the position marker 7*b* according to the present embodiment represents a position at which the compression member 3 can compress the biological tissue with a compression force of a second predetermined value, which is larger than the first predetermined value, or more in the state in which the compression device 1 is attached to the biological surface. That is, the region marker 7*a* indicates the region that can be compressed with the compression force of the first predetermined value or more, and the position marker 7*b* indicates the position that can be compressed with the compression force of the second predetermined value larger than the first predetermined value. Therefore, according to the present embodiment, for example, the medical insertion member 100 (see FIG. 8A) requiring a large compression force, such as a large-diameter sheath, is preferably aligned using the position marker 7*b* in the region marker 7*a*. The above-mentioned compression force of the first predetermined value, the second predetermined value, or the like means a force of a value measured when the compression device 1 is used under a predetermined use condition in a state in which the compression device 1 is appropriately attached to the biological surface. The "predetermined use condition" means a condition determined by a person who manufactures or sells the compression device 1, such as a fluid amount for inflating the inflatable portion 8, which will be described later, of the compression device 1.

As described above, the identification portion 7 according to the present embodiment includes both the region marker 7*a* and the position marker 7*b*, but is not limited to the configuration. The identification portion 7 may be formed of, for example, only one of the region marker 7*a* and the position marker 7*b*.

As described above, the compression device 1 includes the receiving portion 6 and the identification portion 7 of the holding body 5 that is provided at the position adjacent to the receiving portion 6. Therefore, in a state in which a portion of the medical insertion member 100 (see FIG. 8A or the like) inserted into the living body from the biological surface, the portion being exposed to the outside from the biological surface, is received by or in the receiving portion 6, a part or all of the insertion portion 100a (see FIG. 8A or the like) of the medical insertion member 100, which is located on the same surface as the biological surface, can be easily aligned with the identification portion 7. Therefore, the compression device 1 can be easily positioned at an appropriate position on the biological surface.

Hereinafter, details of each member and each portion of the compression device 1 according to the present embodiment will be described.

<Adhesive Sheet 2>

As described above, the adhesive sheet 2 includes the adhesion surface 11 on the one side in the thickness direction A. In addition, the adhesive sheet 2 includes an attachment surface 12 to which the compression member 3 is attached on the other side in the thickness direction A, that is, on the side opposite to the adhesion surface 11. The adhesive sheet 2 has flexibility. Therefore, the adhesive sheet 2 can be deformed according to a shape of the biological surface (i.e., the adhesive sheet 2 can conform to the shape of the biological surface). In addition, the adhesion surface 11 easily follows deformation of the biological surface. As a result, it is possible to prevent the compression device 1 from being unintentionally released from the biological surface.

More specifically, the adhesion surface 11 of the adhesive sheet 2 according to the present embodiment is a lower surface of the adhesive sheet 2. In addition, the attachment surface 12 of the adhesive sheet 2 according to the present embodiment is an upper surface of the adhesive sheet 2.

Hereinafter, for convenience of description, the one side in the thickness direction A, which is a direction from the attachment surface 12 to the adhesion surface 11 in the thickness direction A, may be simply referred to as a "downward direction A1" or a "lower side". In addition, for convenience of description, the other side in the thickness direction A, which is a direction from the adhesion surface 11 to the attachment surface 12 in the thickness direction A, may be simply referred as an "upward direction A2" or an "upper side". Further, in the plan view (see FIGS. 2 and 3) of the compression device 1 seen along the thickness direction A of the adhesive sheet 2, a plan view (see FIG. 2) of the compression device 1 seen from an attachment surface 12 side of the adhesive sheet 2 is simply referred to as a "top view" for convenience of description. In addition, in the plan view (see FIGS. 2 and 3) of the compression device 1 seen along the thickness direction A of the adhesive sheet 2, a plan view (see FIG. 3) of the compression device 1 seen from an adhesion surface 11 side of the adhesive sheet 2 is simply referred to as a "bottom view" for convenience of description. In addition, when the top view and the bottom view are not distinguished from each other, the "plan view" may be simply referred to. In addition, unless otherwise specified, the simple descriptions of the "plan view", the "top view", and the "bottom view" mean a plan view, a top view, and a bottom view when the inflatable portion 8 of the pressing body 4, which will be described later, of the compression member 3 is in a deflated form.

The adhesive sheet 2 is formed by a plurality of layers including, for example, a base material layer and an adhesive layer.

The base material layer is formed of, for example, a thin resin sheet. More specifically, the base material layer is formed of, for example, a white spunlace nonwoven fabric of polyester fibers, and has a thickness in a range of 5 μm to 150 μm, for example, 30 μm. However, a material of the base material layer is not limited to polyester, and for example, an acrylic polymer, polyethylene, an ethylene-vinyl acetate copolymer, polyurethane, a polyamide derivative, and the like may be used.

The adhesive layer is formed of, for example, an adhesive such as a rubber-based adhesive, an acrylic-based adhesive, and a silicon-based adhesive. The adhesive layer is stacked on the base material layer directly or indirectly with another layer interposed therebetween. The adhesion surface 11 of the adhesive sheet 2 according to the present embodiment is an adhesive layer.

The adhesive sheet 2 may further include another layer in addition to the above-mentioned base material layer and the adhesive layer. The adhesive sheet 2 may include, for example, a surface layer. The surface layer is formed of, for example, a resin having a thickness of about 5 μm to 50 μm. More specifically, examples of a material of the surface layer include polyester, polyamide, polyamideimide, polyethylene, polypropylene, polycarbonate, polyurethane, polyvinyl chloride, and fluororesin. The surface layer is stacked on the base material layer directly or indirectly with another layer interposed therebetween on a side opposite to the adhesive layer with the base material layer interposed therebetween. Therefore, the attachment surface 12 of the adhesive sheet 2 may be a surface layer.

More specifically, the adhesive sheet 2 may be formed of a nonwoven fabric tape having an adhesive agent as an adhesive on one surface thereof. Further, the adhesive sheet 2 may be formed of a double-sided tape in which adhesive layers are provided on both sides of the base material layer. When the adhesive sheet 2 is formed of the double-sided tape, the compression member 3 can be fixed to the adhesive sheet 2 by adhering the holding body 5 of the compression member 3 to one adhesive layer of the adhesive sheet.

The adhesive sheet 2 according to the present embodiment has a substantially C-shaped outer shape in the plan view seen in the thickness direction A. As shown in FIGS. 2 and 3, only a part of a lower surface side of the compression member 3 is covered with the adhesive sheet 2 according to the present embodiment. Specifically, only an outer edge region of a lower surface of the compression member 3 is covered with the adhesive sheet 2 according to the present embodiment. The adhesive sheet 2 according to the present embodiment is fixed only to the outer edge region of the lower surface of the compression member 3. In other words, a central region of the lower surface of the compression member 3 in which the inflatable portion 8 of the pressing body 4 of the compression member 3 is located is not covered with the adhesive sheet 2 according to the present embodiment. In addition, the entire outer edge region of the lower surface of the compression member 3 is not covered with the adhesive sheet 2 according to the present embodiment, and a part of the outer edge region is covered with the adhesive sheet 2. That is, a part of the outer edge region of the lower surface of the compression member 3 is not covered with the adhesive sheet 2 according to the present embodiment. According to the present embodiment, a portion of the outer edge region of the lower surface of the compression member 3 which is not covered with the adhesive sheet 2 is a portion adjacent to the receiving portion 6 in the compression member 3.

The adhesion surface 11 of the adhesive sheet 2 is covered with a release sheet in an unused state before being adhered to the biological surface. The release sheet is removed by being released from the adhesion surface 11 by a user when the adhesive sheet 2 is adhered to the biological surface. When the release sheet is removed from the adhesion surface 11 and the adhesion surface 11 is exposed, the adhesion surface 11 of the adhesive sheet 2 is brought into a state of being capable of being adhered to the biological surface (hereinafter, referred to as a "use state" for convenience of description). The release sheet may be formed of, for example, a release paper or a sheet material made of resin. The compression device 1 shown in FIGS. 1 to 6 is in the use state in which the release sheet is removed.

<Compression Member 3>

As described above, the compression member 3 includes the pressing body 4 and the holding body 5.

As described above, the pressing body 4 can press the biological surface by extending in the thickness direction A. The pressing body 4 can press the biological surface at a position where the adhesive sheet 2 is not present in the plan view. That is, the pressing body 4 can press the biological surface without interposing the adhesive sheet 2.

The pressing body 4 according to the present embodiment includes the inflatable portion 8 and an extending portion 9. The inflatable portion 8 is disposed between the biological surface and the holding body 5 in a state in which the adhesion surface 11 of the adhesive sheet 2 is adhered to the biological surface (hereinafter, referred to as an "adhering state of the compression device 1"). The inflatable portion 8 can be inflated in the thickness direction A by supplying a fluid in the adhering state of the compression device 1. That is, the pressing body 4 according to the present embodiment extends in the thickness direction A by inflating the inflatable portion 8 in the thickness direction A. When the inflatable portion 8 is inflated in the adhering state of the compression device 1, the inflatable portion 8 presses the biological surface by receiving a reaction force from the holding body 5. Hereinafter, a form before the inflatable portion 8 is inflated will be referred to as a "deflated form" of the inflatable portion 8. In addition, a form in which the inflatable portion 8 is inflated from the deflated form is referred to as an "inflated form" of the inflatable portion 8. The compression device 1 according to the present embodiment, in the adhering state, does not compress the biological surface by the inflatable portion 8 when the inflatable portion 8 is in the deflated form. On the other hand, the compression device 1 according to the present embodiment, in the adhering state, compresses the biological surface by the inflatable portion 8 when the inflatable portion 8 is in the inflated form. FIG. 5 shows the deflated form of the inflatable portion 8. FIG. 6 shows the inflated form of the inflatable portion 8.

The inflatable portion 8 according to the present embodiment defines accommodation spaces 8*a* in which a fluid such as gas can be accommodated. In addition, the inflatable portion 8 according to the present embodiment includes two balloon portions 8*b* and 8*c* that are connected to each other such that the inside of the balloon portion 8*b* communicates with the inside of the balloon portion 8*c*. The accommodation spaces 8*a* according to the present embodiment are internal spaces in which the two balloon portions 8*b* and 8*c* communicate with each other.

The inflatable portion 8 can be inflated toward the downward direction A1 in the thickness direction A by supplying the fluid to the accommodation spaces 8*a*. The inflatable portion 8 according to the present embodiment is inflated toward the downward direction A1 by changing from the above-mentioned deflated form (see FIG. 5) to the inflated form (see FIG. 6), and is in a posture capable of compressing the biological surface. More specifically, when the fluid is supplied to the accommodation spaces 8*a*, the inflatable portion 8 receives the reaction force from the lower surface of the holding body 5 and is inflated toward the downward direction A1. The fluid supplied to the accommodation spaces 8*a* of the inflatable portion 8 is not limited to gas, and may be a liquid.

As shown in FIG. 5, the inflatable portion 8 in the deflated form is disposed along the lower surface of the holding body 5 in a state in which the accommodation spaces 8*a* are deflated. The accommodation spaces 8*a* of the inflatable portion 8 communicate with a tube 28 extending to the outside of the holding body 5. A fluid such as air is supplied through the tube 28 to the accommodation spaces 8*a* of the inflatable portion 8 from a fluid supply device connected to an inflation port as a connection portion 29 provided at an end portion of the tube 28. Accordingly, the inflated state of the inflatable portion 8 can be changed, and the inflatable portion 8 can be changed from the deflated form (see FIG. 5) to the inflated form (see FIG. 6).

The inflatable portion 8 according to the present embodiment includes a portion having translucency in the thickness direction A. More specifically, the inflatable portion 8 according to the present embodiment is formed by only the portion having translucency in the thickness direction A. Accordingly, it is preferable that the inflatable portion 8 includes at least the portion having translucency in the thickness direction A. Accordingly, a lower side of the inflatable portion 8 can be seen from an upper side of the inflatable portion 8 through the inflatable portion 8. Therefore, a position of the wound or the like on the biological surface can be visually identified through the inflatable portion 8.

The extending portion 9 is extended from the inflatable portion 8. The extending portion 9 has flexibility. The extending portion 9 is wound around the holding body 5. Accordingly, the extending portion 9 extends from the inflatable portion 8 to an upper surface side of the holding body 5 on a side opposite to the inflatable portion 8 with the holding body 5 interposed therebetween. The extending portion 9 is locked to and overlies the holding body 5 on the upper surface side of the holding body 5.

Specifically, the holding body 5 according to the present embodiment defines a through hole 5*a* penetrating in the thickness direction A. The extending portion 9 according to the present embodiment is wound around or overlies the holding body 5 through the through hole 5*a*. More specifically, the extending portion 9 according to the present embodiment extends from a lower side at which the inflatable portion 8 is located with the holding body 5 interposed therebetween toward an upper side opposite to the lower side. The extending portion 9 according to the present embodiment is wound around the holding body 5 along an inner surface of the holding body 5 that defines the through hole 5*a* and the upper surface of the holding body 5. In addition, the extending portion 9 is formed with a locking hole 9*b* on the upper surface side of the holding body 5. A locking protrusion 5*b* protruding from the upper surface of the holding body 5 is fitted into the locking hole 9*b*. The extending portion 9 is positioned on the holding body 5 by fitting the locking protrusion 5*b* into the locking hole 9*b*. In addition, the extending portion 9 is wound from a lower surface side to the upper surface side of the holding body 5 at a position on a receiving portion 6 side with respect to the inflatable portion 8. That is, the through hole 5a according to the present embodiment is located on the receiving portion 6 side with respect to the inflatable portion 8. Therefore, in a cross-sectional view shown in FIG. 5, the inflatable portion 8 and the extending portion 9 that constitute the pressing body 4 according to the present embodiment are curved in a substantially U shape by being wound around the holding body 5. Accordingly, the inflatable portion 8 can be inflated while pivoting about a portion of the extending portion 9 which is connected to the inflatable portion 8 as a hinge portion 9a.

The inflatable portion 8 can be inflated not only toward the thickness direction A but also toward a direction inclined with respect to the thickness direction A by pivoting about the hinge portion 9a of the extending portion 9. As described above, the pressing body 4 according to the present embodiment is fixed to the holding body 5 in a state in which the extending portion 9 having a sheet shape is wound around the upper and lower surfaces of the holding body 5 through the through hole 5a of the holding body 5. Therefore, at the time of inflating, the inflatable portion 8 is inflated while pivoting about the hinge portion 9a, which is the portion of the extending portion 9 which is connected to the inflatable portion 8 on a lower side of the through hole 5a, as a pivot center. More specifically, the two balloon portions constituting the inflatable portion 8 according to the present embodiment overlap with each other in the thickness direction A. In addition, one end of each of the two balloon portions is attached to the extending portion 9. That is, one end side of each of the two balloon portions is restrained by the extending portion 9. Therefore, even when the two balloon portions are inflated, the two balloon portions are not separated from each other on the one end side. On the other hand, the other end side of each of the two balloon portions is not restrained at all. Therefore, when the two balloon portions are inflated, the two balloon portions are separated from each other on the other end side. That is, in the two balloon portions constituting the inflatable portion 8 according to the present embodiment, the other end side, which is not attached to the extending portion 9, pivots about a pivot center with the one end side attached to the extending portion 9 as the pivot center. Accordingly, the inflatable portion 8 according to the present embodiment is inflated toward the direction inclined with respect to the thickness direction A. Perforations P (see FIG. 12B) to be described later are easily narrowed or obstructed by inflating the inflatable portion 8 toward the direction inclined with respect to the thickness direction A. The details will be described later (see FIG. 13). Alternatively, a configuration for inflating the inflatable portion 8 toward the direction inclined with respect to the thickness direction A is not limited to a configuration of the pressing body 4 according to the present embodiment.

The extending portion 9 according to the present embodiment includes a portion having translucency in the thickness direction A at a position at which the upper surface of the holding body 5 is covered. Specifically, an entire portion of the extending portion 9 according to the present embodiment with which the upper surface of the holding body 5 is covered has translucency in the thickness direction A. More specifically, the extending portion 9 according to the present embodiment has the sheet shape, and has translucency in a thickness direction at any position. Alternatively, the extending portion 9 may include a portion having translucency in the thickness direction in, for example, only a part at the position at which the upper surface of the holding body 5 is covered.

Constituent materials from which the inflatable portion 8 and the extending portion 9 of the pressing body 4 may be fabricated include, for example, soft polyvinyl chloride, polyurethane, polyethylene, polypropylene, polyester, ethylene-vinyl acetate copolymer (EVA), silicone, or a material having flexibility obtained by mixing any of these materials.

The holding body 5 includes a main body portion 31 that is flat and has a substantially quadrangular shape in the plan view, and a pair of gripping plate portions 32 that protrude from the main body portion 31 in the upward direction A2 and that face each other.

The main body portion 31 is formed with the above-mentioned through hole 5a. In addition, the main body portion 31 includes the above-mentioned locking protrusion 5b fitted into the locking hole 9b of the extending portion 9 of the pressing body 4. The above-mentioned inflatable portion 8 of the pressing body 4 is disposed at a lower surface side of a central portion of the main body portion 31.

The main body portion 31 is fixed to the attachment surface 12 of the adhesive sheet 2. Specifically, only an outer edge portion of a lower surface of the main body portion 31 is fixed to the attachment surface 12 of the adhesive sheet 2 having a substantially C shape in the plan view. The central portion of the lower surface of the main body portion 31 is not covered with the adhesive sheet 2. Therefore, the central portion of the lower surface of the main body portion 31 is not fixed to the attachment surface 12 of the adhesive sheet 2.

The main body portion 31 of the holding body 5 is provided with the identification portion 7. By providing the identification portion 7, the inflatable portion 8 can appropriately compress a compression position on the biological tissue to be pressed and compressed by the inflatable portion 8 of the pressing body 4. Specifically, the identification portion 7 according to the present embodiment indicates a place where the biological tissue can be compressed with a compression force of a predetermined value or more by the inflatable portion 8 in the top view (see FIG. 2) of the compression device 1 in a state of being attached to the biological surface. Therefore, the compression device 1 is attached to the biological surface such that the identification portion 7 overlaps with a predetermined compression position on the biological surface. Accordingly, the predetermined compression position on the biological surface can be appropriately compressed by the compression device 1. At least a part of the identification portion 7 according to the present embodiment is provided at a position overlapping with the inflatable portion 8 of the pressing body 4 in the plan view seen in the thickness direction A. Therefore, at least a part of the identification portion 7 overlapping with the inflatable portion 8 in the thickness direction A may be aligned to overlap with the predetermined compression position on the biological surface in the plan view. Accordingly, by providing the identification portion 7, the compression device 1 can be easily attached to the appropriate position on the biological surface.

The identification portion 7 according to the present embodiment is provided on an upper surface of the main body portion 31 of the holding body 5. Therefore, it is easy for a health care worker who is operating the compression device 1 to visually identify the identification portion 7 according to the present embodiment. Alternatively, the identification portion 7 may be provided inside the holding body 5. Further, the identification portion 7 may be provided on the lower surface of the main body portion 31 of the holding body 5. Details of the configuration in which the identification portion 7 is provided on the lower surface of the holding body 5 will be described later (see FIG. 10).

As described above, the configuration of the identification portion 7 is not particularly limited as long as the identification portion 7 can be visually identified in the plan view. Therefore, a shape or mode of the identification portion 7 in the plan view is not particularly limited.

As described above, the identification portion 7 according to the present embodiment includes the region marker 7*a* and the position marker 7*b*. The region marker 7*a* according to the present embodiment is a frame line marker that surrounds the portion having translucency in the thickness direction A. The frame line marker as the region marker 7*a* can be implemented, for example, by a part of the upper surface of the main body portion 31 of the holding body 5 formed of a resin kneaded with a dye, a colored paint, and the like. A color of the frame line marker as the region marker 7*a* is not particularly limited, and is preferably a green-based color. By using the green-based color, the health care worker or the like can easily and visually identify the frame line marker on blood or the biological surface. Therefore, it is easier to align the inflatable portion 8 with the compression position on the biological surface by using the frame line marker as the region marker 7*a*. In addition, the frame line marker as the region marker 7*a* may be constituted by a convex portion protruding from the upper surface of the holding body 5 or a concave portion such as a groove portion formed on the upper surface of the holding body 5.

The frame line marker as the region marker 7*a* according to the present embodiment has a rectangular shape, but the shape is not particularly limited. The frame line marker may have, for example, a circular shape, an oval shape, and a polygonal shape other than a square shape. In addition, a part of the frame line marker as the region marker 7*a* according to the present embodiment is divided by the through hole 5*a* of the holding body 5, but is not limited thereto. The frame line marker may be provided only on a side opposite to the receiving portion 6 side with respect to the through hole 5*a*. As shown in FIG. 1 for example, the visually identifiable line constituting the region marker 7*a* is generally U-shaped and open at one end, specifically the end facing towards the receiving portion 6.

The region marker 7*a* is not limited to the frame line marker that defines a predetermined region by a frame line. The region marker 7*a* may have a configuration in which the predetermined region is bordered by an outer edge of a region filled with a predetermined color.

The position marker 7*b* according to the present embodiment is a line segment marker that is curved and extends in an arc shape in the plan view seen in the thickness direction A. The line segment marker as the position marker 7*b* can be implemented, for example, by a part of the upper surface of the main body portion 31 of the holding body 5 formed of a resin kneaded with a dye, a colored paint, and the like. A color of the line segment marker as the position marker 7*b* is not particularly limited, and is preferably a green-based color. By using the green-based color, the health care worker or the like can easily and visually identify the line segment marker on blood or the biological surface. The line segment marker as the position marker 7*b* may be constituted by a convex portion protruding from the upper surface of the holding body 5 or a concave portion such as a groove portion formed on the upper surface of the holding body 5. As shown in FIG. 1 for example, the visually identifiable line constituting the position marker 7*b* is generally U-shaped and open at one end, specifically the end facing towards the receiving portion 6.

By using the position marker 7*b* as the line segment marker, regardless of an outer diameter of the medical insertion member 100 (see FIG. 8A) in a state of being inserted into the living body from the biological surface, a part (for example, a part of the outer surface) of the insertion portion 100*a* (see FIG. 8A) of the medical insertion member 100, which is located on the same surface as the biological surface, can be aligned to come into contact with or overlap with the line segment marker in the plan view. That is, unlike the region marker 7*a*, the position marker 7*b* does not define a predetermined closed region in the plan view. Therefore, even the medical insertion member 100 including the insertion portion 100*a* that does not match an area or an outer edge contour of a region of the region marker 7*a* can be aligned with the line segment marker as the position marker 7*b* by using a part of the insertion portion 100*a*. Here, a "medical insertion member including an insertion portion that does not match an area or an outer edge contour of a region of a region marker" includes, for example, a medical insertion member having an outer diameter that does not fit in a region, and a medical insertion member having an outer diameter that can fit a plurality of the medical insertion members in a region. That is, by using the position marker 7*b* as a line segment marker that does not define a predetermined region, it is possible to perform the alignment regardless of the outer diameter of the medical insertion member 100 (see FIG. 8A) in the state of being inserted into the living body from the biological surface.

A shape of the line segment marker as the position marker 7*b* in the plan view is not particularly limited. The line segment marker as the position marker 7*b* according to the present embodiment extends in the arc shape in the plan view. With the line segment marker having such a shape, it is easy to align the insertion portion 100*a* extending in an arc shape in a convex shape in the plan view such that a part of the outer surface of the insertion portion 100*a* enters a concave portion of the line segment marker. Therefore, the shape of the line segment marker as the position marker 7*b* in the plan view is not particularly limited, may be an extending linear shape, and preferably has a concave portion such as an arc shape or a V shape according to the present embodiment.

The position marker 7*b* is not limited to the line segment marker. The position marker 7*b* may be, for example, a point marker (see FIG. 9B). Further, the position marker 7*b* may be formed of an aggregate of point markers. An example of the aggregate of the point markers is a broken line marker formed of point markers arranged in a row.

The identification portion 7 of the main body portion 31 of the holding body 5 may have a non-transparent configuration in the thickness direction A, and is preferably semi-transparent or transparent having translucency in the thickness direction A. Specifically, the region marker 7*a* and the position marker 7*b* according to the present embodiment are preferably semi-transparent or transparent having translucency in the thickness direction A. Accordingly, the health care worker can visually identify a degree of overlap between the identification portion 7 and the position on the biological surface to be aligned with the identification portion 7.

It is preferable that the periphery of the identification portion 7 of the main body portion 31 of the holding body 5 has translucency in the thickness direction A. It is preferable that the holding body 5 according to the present embodiment includes a portion having translucency in the thickness direction A in an adjacent periphery outside the region marker 7a in the plan view seen in the thickness direction A. Further, it is preferable that a portion inside the region marker 7a in the plan view seen in the thickness direction A and excluding the position marker 7b in the holding body 5 according to the present embodiment has translucency in the thickness direction A. In other words, it is preferable that the frame line marker as the region marker 7a of the holding body 5 according to the present embodiment borders a part of a region of the portion having translucency of the holding body 5 in the thickness direction A. Accordingly, when the health care worker performs an operation of moving the compression device 1 along the biological surface such that the identification portion 7 overlaps with a predetermined position on the biological surface, the health care worker can move the compression device 1 while visually identifying the position on the biological surface through the portion having translucency in the periphery of the identification portion 7. That is, since the periphery of the identification portion 7 of the main body portion 31 of the holding body 5 is constituted by the portion having translucency in the thickness direction A, an operation of attaching the compression device 1 to the appropriate position on the biological surface becomes easier.

As described above, the inflatable portion 8 and the extending portion 9 of the pressing body 4 according to the present embodiment also have translucency in the thickness direction A. In the compression device 1 according to the present embodiment, the extending portion 9 of the pressing body 4, the identification portion 7 of the holding body 5 and the periphery thereof, and the inflatable portion 8 of the pressing body 4 are stacked in the thickness direction A. Hereinafter, this part is referred to as a "stacked portion". It is preferable that the stacked portion according to the present embodiment is formed by stacking the portions having translucency. Accordingly, in the compression device 1 according to the present embodiment, it is possible to visually identify one side from the other side in the thickness direction A through the extending portion 9 of the pressing body 4, the identification portion 7 of the holding body 5 and the periphery thereof, and the inflatable portion 8 of the pressing body 4. As a result, according to the compression device 1 according to the present embodiment, the alignment of the identification portion 7 on the biological surface becomes easier. As described above, when the entire stacked portion is constituted by portions having translucency, it is preferable that the identification portion 7 can be identified with respect to all the other layers of the stacked portion in the plan view. Accordingly, the alignment of the identification portion 7 on the biological surface becomes easier.

A method for providing the identification portion 7 is not particularly limited, and for example, printing, fusion, adhesion, and integral molding can be used.

At least a part of the identification portion 7 according to the present embodiment is provided at a position between the pair of gripping plate portions 32 in the plan view. Accordingly, the health care worker who operates the compression device 1 can easily and visually identify the identification portion 7 in a state of gripping the pair of gripping plate portions 32 to sandwich the pair of gripping plate portions 32 from two sides. Therefore, an operability of the compression device 1 is improved. More specifically, according to the present embodiment, a part of the region marker 7a and the entire position marker 7b of the identification portion 7 are disposed between the pair of gripping plate portions 32 in the plan view.

The pair of gripping plate portions 32 are gripped by the health care worker. By providing the pair of gripping plate portions 32, the compression device 1 can be easily held. Therefore, it is possible to improve the operability for the health care worker.

Examples of a material of the holding body 5 according to the present embodiment include a resin material. Examples of the resin material include thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, and polyethylene terephthalate, and thermosetting resins such as phenol resin, epoxy resin, silicone resin, and unsaturated polyester.

It is preferable that at least the central portion of the main body portion 31 of the holding body 5 is formed of a material having ultrasonic transmissibility. In addition, it is preferable that the above-mentioned pressing body 4 is also formed of a material having ultrasonic transmissibility. Further, as the fluid supplied to the accommodation spaces 8a of the inflatable portion 8 of the pressing body 4, a fluid having ultrasonic transmissibility such as water or gel is used. Accordingly, an obstructed state of the blood vessel made by the compression device 1 can be detected by an ultrasonic device. The details will be described later.

<Compression Method Using Compression Device 1>

Figure 7:
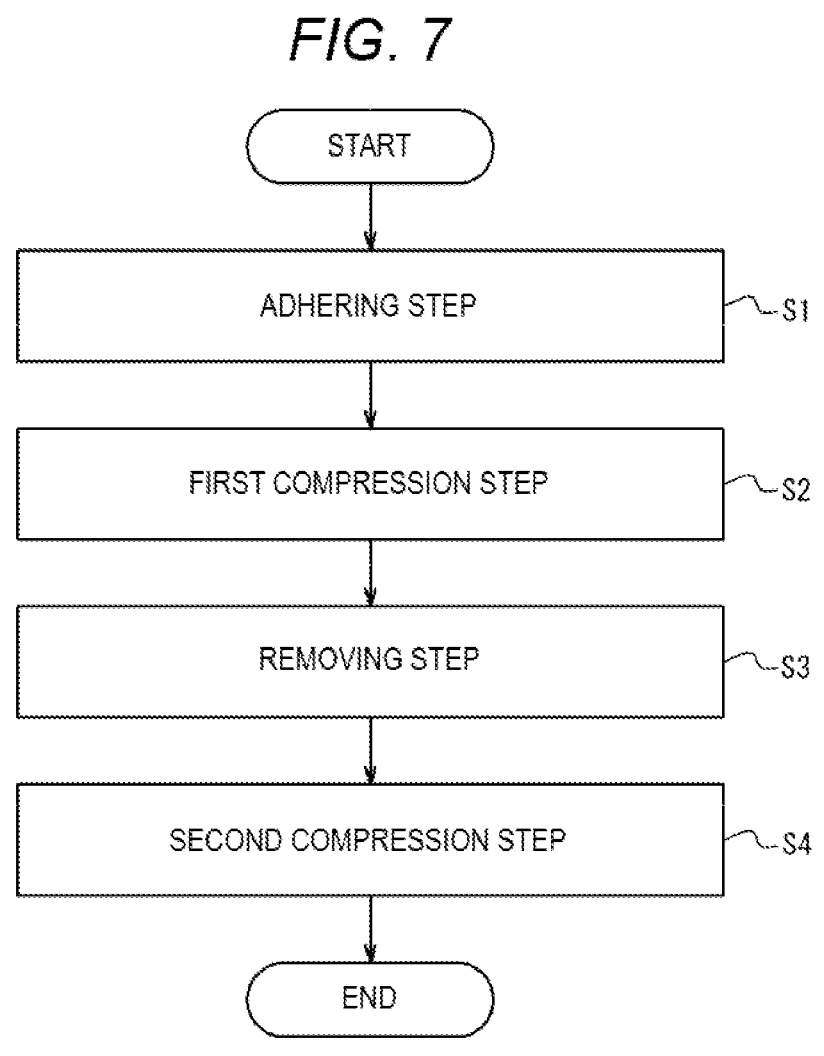
Figure 8A:
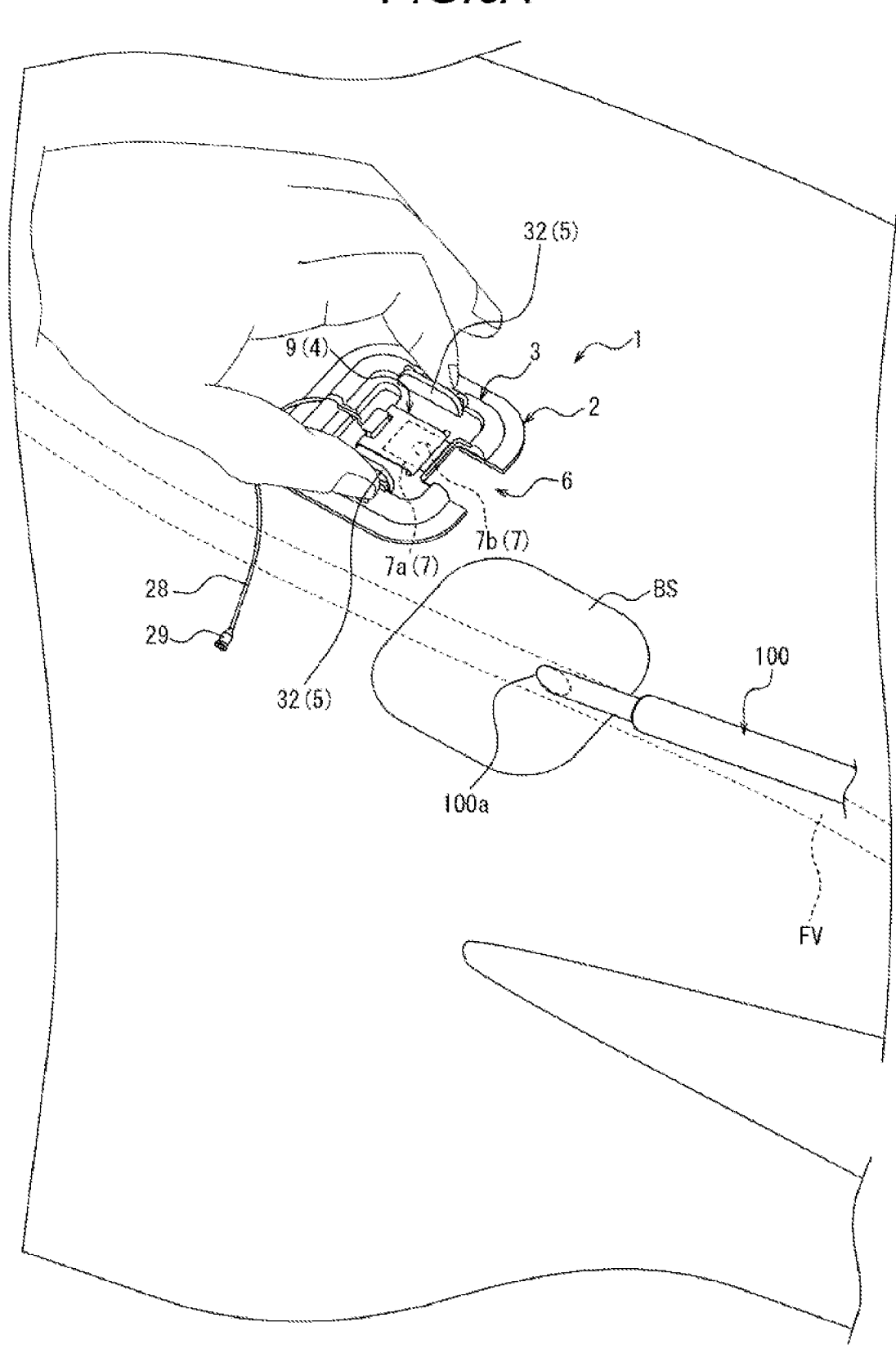
FIG. 8A is a diagram showing an outline of an adhering step in FIG. 7.
Figure 8B:
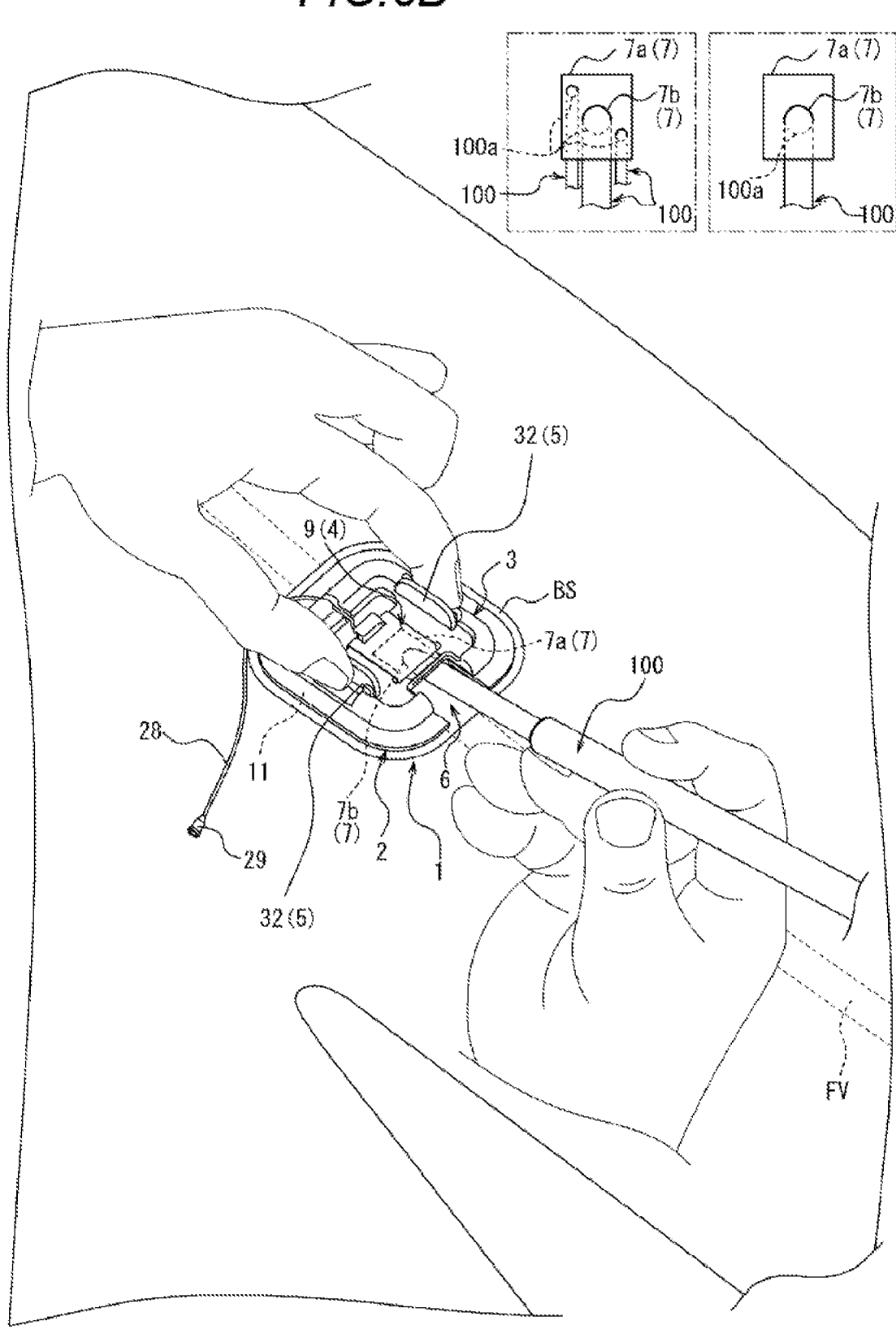
FIG. 8B is a diagram showing an outline of the adhering step in FIG. 7.
Figure 8C:
FIG. 8C is a diagram showing an outline of a first compression step in FIG. 7.
Figure 8D:
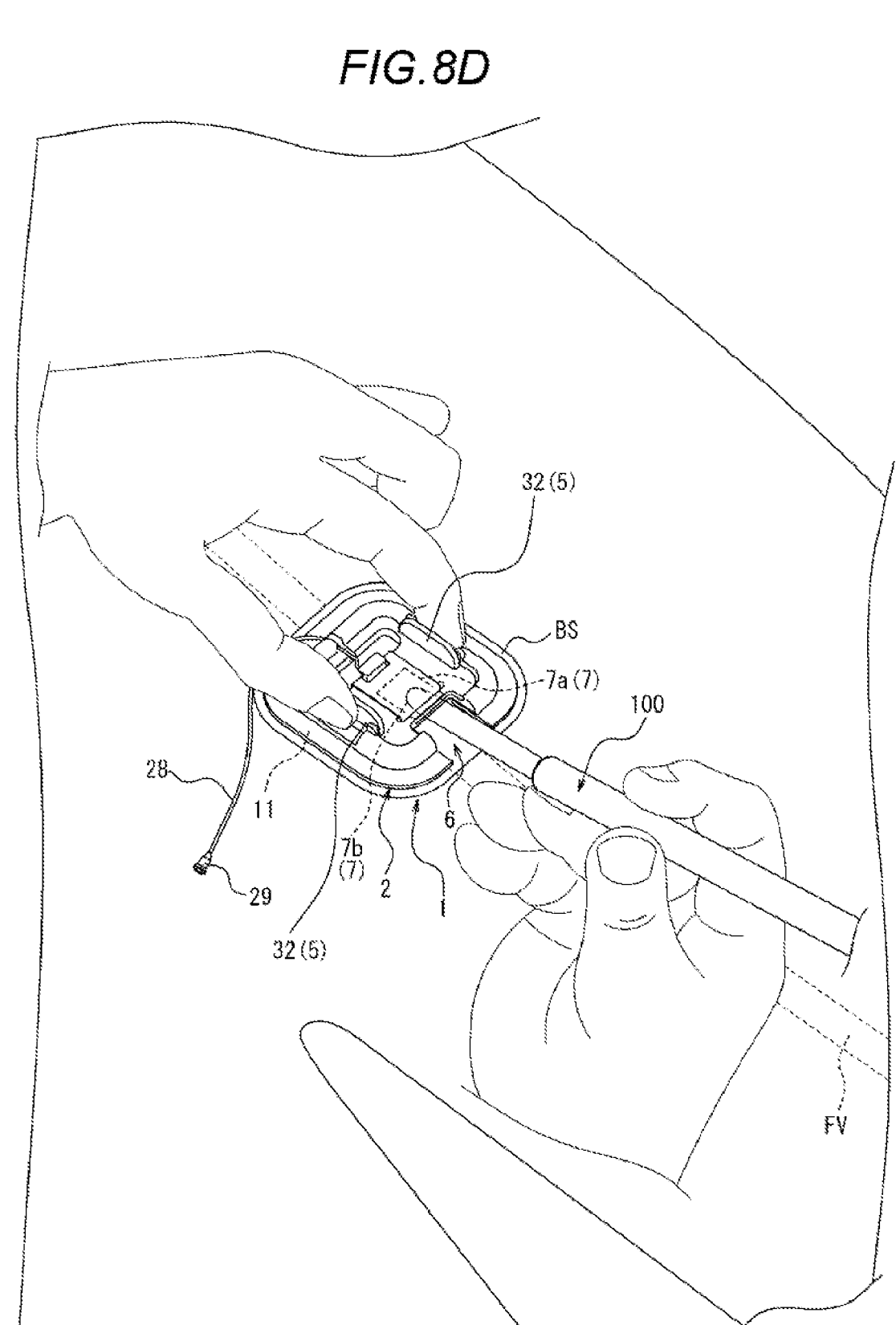
FIG. 8D is a diagram showing an outline of a removing step in FIG. 7.
Figure 8E:
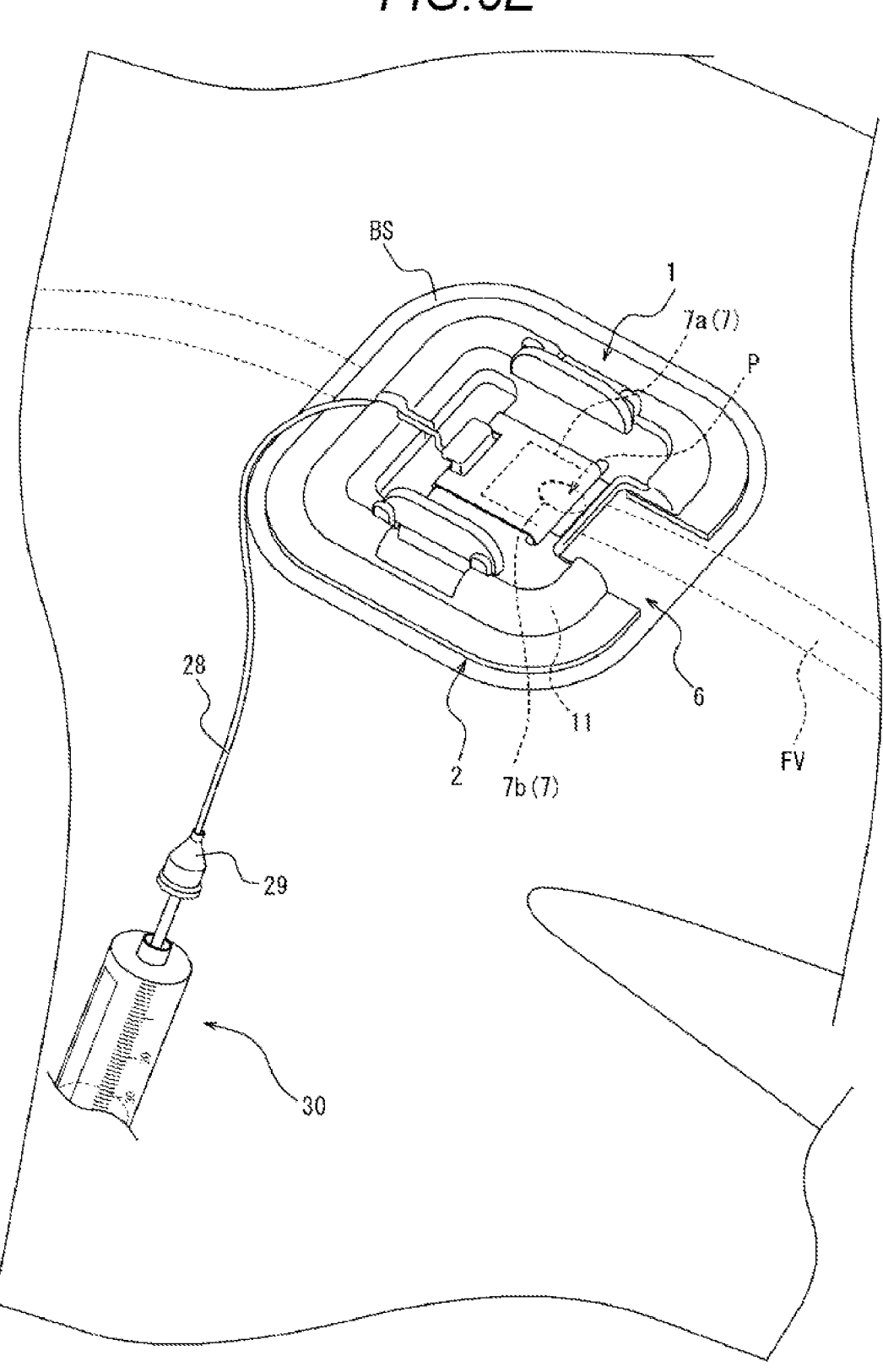
FIG. 8E is a diagram showing an outline of a second compression step in FIG. 7.

Next, a method for compressing a biological surface using the compression device 1, the method including an example of a method for adhering the compression device 1 according to this disclosure, will be described. FIG. 7 is a flowchart showing an example of the method for compressing the biological surface. The compression method shown in FIG. 7 includes an adhering step S1, a first compression step S2, a removing step S3, and a second compression step S4. FIGS. 8A and 8B are diagrams showing an outline of the adhering step S1. FIG. 8C is a diagram showing an outline of the first compression step S2. FIG. 8D is a diagram showing an outline of the removing step S3. FIG. 8E is a diagram showing an outline of the second compression step S4.

Figure 12A:
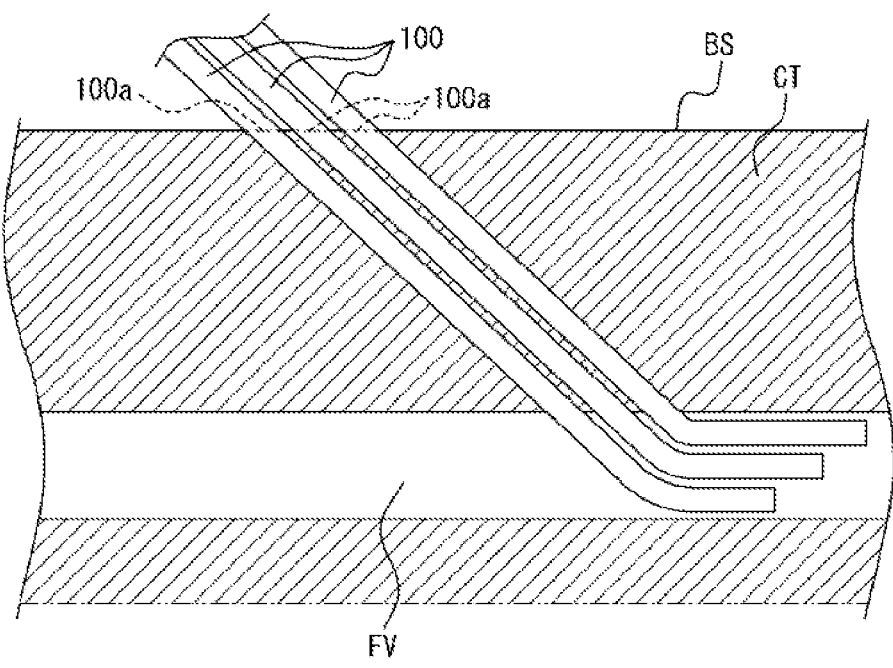
FIG. 12A is a diagram showing a state in which a medical insertion member is inserted into a femoral vein from the biological surface through a connective tissue.
Figure 12B:
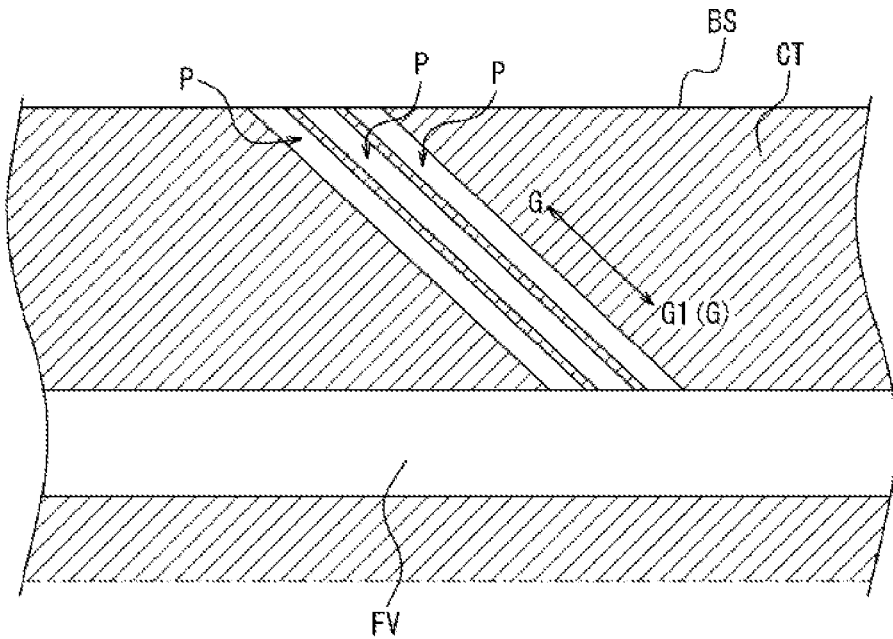
FIG. 12B is a diagram showing a state after the medical insertion member is removed from the state shown in FIG. 12A.

The compression method shown in FIGS. 7 to 8E is a method for compressing a biological surface BS to narrow or obstruct a perforation leading from the biological surface to a vein without obstructing the vein. The perforation is formed by removing a sheath as the medical insertion member 100 in a state of being inserted into a vein such as a femoral vein from the biological surface BS through a connective tissue. By the compression method shown here, bleeding can be stopped after the sheath as the medical insertion member 100 is removed. First, the perforation formed after the medical insertion member 100 is removed will be described with reference to FIGS. 12A and 12B. FIG. 12A shows a state in which the sheath as the medical insertion member 100 is inserted into a femoral vein FV from the biological surface BS through a connective tissue CT. FIG. 12A shows three sheaths as the medical insertion members 100, and the number of sheaths may be two or less, or may be four or more. FIG. 12B shows a state after the sheaths as the medical insertion members 100 are removed from the state shown in FIG. 12A. As shown in FIG. 12B, when the sheaths as the medical insertion members 100 are removed, the perforations P are formed between the biological surface BS and the femoral vein FV. In the compression method shown in FIGS. 7 to 8E, the perforations P can be narrowed or obstructed without obstructing the femoral vein FV. Therefore, even when bleeding from a vein located at a deep position from the biological surface is stopped, bleeding can be stopped more efficiently without narrowing or obstructing the vein itself. Hereinafter, the details of the steps S1 to S4 will be described with reference to FIGS. 8A to 8E.

FIG. 8A shows a state in which the sheath as the medical insertion member 100 is inserted from the biological surface BS into the femoral vein FV (see FIGS. 12A and 12B). FIG. 8B shows a state in which the attachment of the compression device 1 to a predetermined position on the biological surface BS is completed in a state in which the sheath as the medical insertion member 100 is inserted into the living body. In addition, FIG. 8B shows the details of the alignment between the identification portion 7 and the insertion portion 100a of the medical insertion member 100 in the plan view in an enlarged manner within frames of two-dot chain lines. FIGS. 8A and 8B show the use state of the compression device 1 after the release sheet is released from the adhesion surface 11.

As shown in FIGS. 8A and 8B, the compression device 1 is attached to the biological surface by adhering the adhesion surface 11 of the adhesive sheet 2 on the biological surface. Specifically, as shown in FIG. 8B, the adhesive sheet 2 is adhered to the biological surface BS in a state in which a portion of the sheath as the medical insertion member 100 inserted into the living body from the biological surface BS, the portion being exposed to the outside from the biological surface BS, is received by or in the receiving portion 6. Further, as shown in FIG. 8B, the insertion portion 100a of the sheath as the medical insertion member 100, which is located on the same surface as the biological surface BS, is aligned with the identification portion 7 (see the frames of the two-dot chain lines in FIG. 8B). The adhesive sheet 2 is adhered to the biological surface BS in such an aligned state.

More specifically, as shown in FIG. 8B, according to the present embodiment, the whole insertion portion 100a of the sheath as the medical insertion member 100, which is located on the same surface as the biological surface BS, is aligned within the region marker 7a of the identification portion 7. The adhesive sheet 2 is adhered to the biological surface BS in such an aligned state. By providing the region marker 7a, as shown in the enlarged manner in the frame of the two-dot chain line on a left side in FIG. 8B, even when a plurality of (three in the frame of the two-dot chain line on the left side in FIG. 8B) the medical insertion members 100 are inserted into the living body, all the insertion portions 100a can be aligned to fit within the region of the region marker 7a. Accordingly, the compression device 1 can be easily attached to an appropriate position on the biological surface BS at which all the insertion portions 100a of the plurality of medical insertion members 100 can be compressed with a predetermined compression force. In addition, as shown in FIG. 8B, according to the present embodiment, a thin sheath having an outer diameter less than a predetermined value or the like is not aligned with the position marker 7b in the region marker 7a (see the frame of the two-dot chain line on the left side in FIG. 8B), and a part of the outer surface of the insertion portion 100a of a thick sheath having an outer diameter equal to or higher than the predetermined value or the like is aligned with the position marker 7b in the region marker 7a (see the frames of the two-dot chain lines on the left and right sides in FIG. 8B). As described above, the position marker 7b according to the present embodiment indicates a position in the region of the region marker 7a at which a particularly large compression force can be obtained. Therefore, for example, even in a case of a large-diameter sheath or the like that requires a large compression force, a predetermined compression force can be secured. In addition, for example, even when both the large-diameter sheath that requires the large compression force and a small-diameter sheath thinner than the large-diameter sheath are provided (see the frame of the two-dot chain line on the left side in FIG. 8B), the large-diameter sheath is aligned with the position marker 7b in the region marker 7a, and the small-diameter sheath is not aligned with the position marker 7b in the region marker 7a, and thus a desired compression force required for each sheath can be implemented based on a difference in compression forces in the region marker 7a. Accordingly, after various alignments are performed, the adhesive sheet 2 is adhered to the biological surface BS. By providing the position marker 7b in addition to the region marker 7a, the compression device 1 can be easily attached to a more appropriate position on the biological surface BS in consideration of the difference in the compression forces within the region of the region marker 7a.

As described above, the position marker 7b according to the present embodiment is the line segment marker that is curved and extends in the arc shape in the plan view seen in the thickness direction A. Therefore, according to the present embodiment, a part of the outer surface of the insertion portion 100a of the medical insertion member 100 is aligned to come into contact with or overlap with the line segment marker as the position marker 7b in the plan view. The compression device 1 is attached to the biological surface BS in such an aligned state.

Next, as shown in FIG. 8C, a syringe 30 as the fluid supply device is connected to the connection portion 29 of the tube 28. Through the tube 28, air is supplied to the accommodation spaces 8a (see FIG. 6) of the inflatable portion 8 of the pressing body 4 of the compression device 1 to inflate the inflatable portion 8. Accordingly, before the sheath as the medical insertion member 100 is removed from the biological surface BS, the vicinity of a wound on the biological surface BS can be compressed in advance. In other words, compression on the biological surface BS is started in a state in which the sheath as the medical insertion member 100 is inserted into the femoral vein FV as a vein from the biological surface BS through the connective tissue CT (see FIGS. 12A and 12B). In this way, the medical insertion member 100 is compressed before being removed from the biological surface BS. Accordingly, immediately after the sheath as the medical insertion member 100 is removed, the biological surface BS can be compressed. Therefore, the perforations P (see FIG. 12B) extending from the biological surface BS to the femoral vein FV (see FIGS. 12A and 12B) can be narrowed or obstructed immediately after the sheaths are removed.

Next, as shown in FIG. 8D, the sheath as the medical insertion member 100 is removed from the biological surface BS. The perforations P shown in FIG. 12B are formed by removing the sheaths. When the biological surface BS is not compressed at all in this state, bleeding from the femoral vein FV to the outside of the living body through the perforations P and the wound on the biological surface BS occurs. However, in the compression method shown here, as shown in FIG. 8C, the biological surface BS is compressed in advance before the sheath as the medical insertion member 100 is removed from the biological surface BS. Therefore, immediately after the sheaths are removed, the biological surface BS can be compressed to narrow or obstruct the perforations P (see FIG. 12B), and the amount of bleeding immediately after the sheaths are removed can be reduced.

Next, as shown in FIG. 8E, the syringe 30 as the fluid supply device is connected again to the connection portion 29 of the tube 28. Air is supplied again to pressurize the accommodating spaces 8a of the inflatable portion 8 of the compression device 1 through the tube 28, or the air is evacuated from the accommodating spaces 8a to reduce the pressure. In other words, the compression force on the biological surface BS is adjusted after the sheath as the medical insertion member 100 is removed. Accordingly, by adjusting the compression force on the biological surface BS and further narrowing or obstructing the perforations P (see FIG. 12B) without obstructing the femoral vein FV (see FIGS. 12A and 12B), the amount of bleeding can be greatly reduced or the bleeding can be stopped.

More specifically, when the bleeding is confirmed after the sheaths are removed, the compression force is slowly increased to pressurize until the bleeding is stopped. On the other hand, when the bleeding is confirmed to be stopped after the sheaths are removed, the compression force is slowly reduced to reduce the pressure until the bleeding is confirmed. After the bleeding is confirmed, the compression force is slowly increased to pressurize until the bleeding is stopped. Accordingly, it is possible to prevent the obstruction of the femoral vein FV (see FIGS. 12A and 12B) due to excessive pressurization.

Whether the biological surface BS is appropriately compressed may be detected using the ultrasonic device. Specifically, the pressing body 4 and the holding body 5 are formed of a material having ultrasonic transmissibility, and by supplying the fluid having ultrasonic transmissibility such as water to the inflatable portion 8 of the pressing body 4, a compression state made by the compression device 1 can be diagnosed by ultrasounds. That is, the ultrasonic device can detect whether the femoral vein FV (see FIGS. 12A and 12B) is obstructed. The compression force of the compression device 1 may be adjusted based on a diagnosis result by the ultrasonic device.

By maintaining the compression state for several hours (for example, 2 to 6 hours) as it is, the bleeding can be stopped. After the bleeding is stopped, the compression device 1 is removed from the biological surface BS by releasing the adhesion surface 11 of the adhesive sheet 2 from the biological surface BS.

In the compression method shown here, the perforations P (see FIG. 12B) are narrowed or obstructed without obstructing the femoral vein FV (see FIGS. 12A and 12B). When the bleeding from the vein is stopped, the bleeding can be stopped by narrowing or obstructing the perforations P (see FIG. 12B). On the other hand, for example, when bleeding from a femoral artery is stopped, even when only the perforations are obstructed, the blood leaks and spreads in the connective tissue CT (see FIGS. 12A and 12B), and thus the bleeding cannot be stopped. When stopping the bleeding from the femoral artery, it is necessary to take a large measure, such as a method for strongly compressing the artery itself until the artery is narrowed or obstructed, or a method for obstructing a hole of an artery wall.

Therefore, in the above-mentioned compression methods, it is preferable to compress the biological surface BS to a position at which a compression depth from the biological surface BS is 5 mm to 20 mm. By setting the compression depth within the above-mentioned range, it is easy to implement the compression state in which the perforations P (see FIG. 12B) are narrowed or obstructed without obstructing the vein. The compression depth is more preferably 5 mm to 15 mm, and even more preferably 8 mm to 12 mm.

In the above-mentioned compression methods, it is preferable to compress the biological surface BS at 10 g/cm2 to 600 g/cm2 from the biological surface BS. Compression pressure is pressure after the sheath as the medical insertion member 100 is removed, and does not mean the above-mentioned compression force before the sheath is removed. By setting the compression pressure in the above-mentioned range, it is easy to implement the compression state in which the perforations P (see FIG. 12B) are narrowed or obstructed without obstructing the vein. The compression pressure is more preferably 50 g/cm2 to 400 g/cm2, and even more preferably 100 g/cm2 to 300 g/cm2.

It is preferable to compress the biological surface BS along a direction orthogonal to an extending direction of the perforations P (see FIG. 12B). The phrase "compressing the biological surface BS along a direction orthogonal to an extending direction of the perforations" means not only compressing only in the direction orthogonal to the extending direction of the perforations but also compressing in a direction inclined at an angle equal to or less than a predetermined angle (for example, 30 degrees or less) with respect to the direction orthogonal to the extending direction of the perforations. The compression device 1 according to the present embodiment can compress the biological surface BS along the direction orthogonal to the extending direction of the perforations P (see FIG. 12B).

Figure 13:
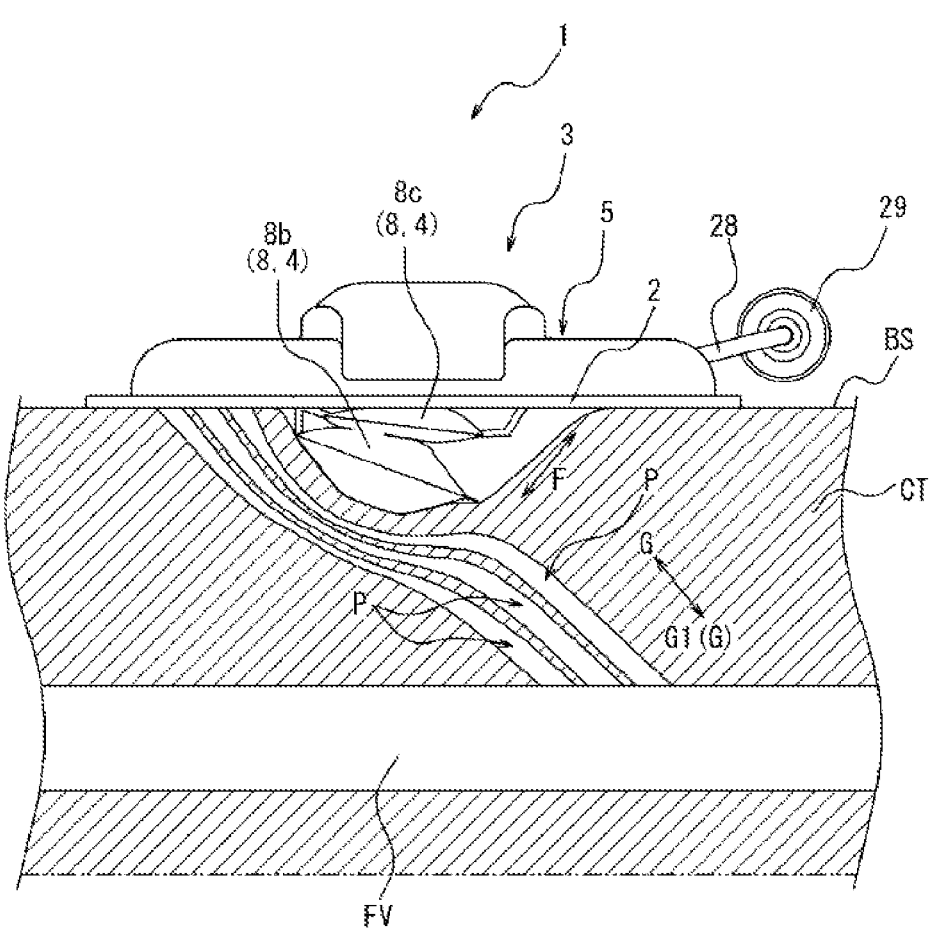
FIG. 13 is a diagram showing a state in which perforations shown in FIG. 12B are narrowed or obstructed by the compression device shown in FIG. 1.
Figure 13:

Specifically, as described above, the inflatable portion 8 of the pressing body 4 according to the present embodiment can be inflated toward the direction inclined with respect to the thickness direction A. Accordingly, the biological surface can be compressed along the direction orthogonal to the extending direction of the perforations P (see FIG. 12B). Specifically, as shown in FIGS. 12A and 12B, the sheath as the medical insertion member 100 is inserted not in a direction orthogonal to the biological surface BS (the same direction as the thickness direction A) but in a direction inclined to one side with respect to the direction orthogonal to the biological surface BS. Therefore, as shown in FIG. 12B, the extending direction of the perforations P is also inclined with respect to the direction orthogonal to the biological surface BS. Therefore, when the inflatable portion 8 can be inflated in a direction inclined to a side opposite to the extending direction of the perforations P (hereinafter, may be referred to as an "inclination direction F") with respect to the thickness direction A which is the direction orthogonal to the biological surface BS, the biological surface BS is easily compressed along the direction orthogonal to the extending direction of the perforations P. Accordingly, it is easy to implement the compression device 1 that narrows or obstructs the perforations P without obstructing the vein such as the femoral vein FV in FIGS. 12A and 12B. FIG. 13 is a diagram showing the state in which the perforations P shown in FIG. 12B are narrowed or obstructed by the compression device 1. As shown in FIG. 13, the perforations P are more easily narrowed or obstructed without further obstructing the vein such as the femoral vein FV by the compression device 1.

According to the compressing method shown in FIGS. 7 to 8E, the bleeding can be stopped by narrowing or obstructing the perforations P (see FIG. 12B) without obstructing the vein such as the femoral vein FV. In particular, by implementing the above-mentioned compression method using the compression device 1, it is possible to stop the bleeding by a simple method without compression by a hand of the health care worker or using a large-scale hemostasis device.

<Compression of Compression Device 1 on Biological Surface>

As shown in FIG. 13, in the compression device 1, the inflatable portion 8 of the pressing body 4 of the compression member 3 can compress the biological surface toward the inclination direction F inclined with respect to a vertical direction (in FIG. 13, the vertical direction is the same direction as the thickness direction A, and is an upward-downward direction in FIG. 13.) Hereinafter, it is simply referred to as a "vertical direction".) perpendicular to the biological surface BS in a state in which the adhesive sheet 2 is attached to the living body. Accordingly, as shown in FIG. 13, the perforations P are easily narrowed or obstructed without obstructing the vein such as the femoral vein FV.

Figure 14:
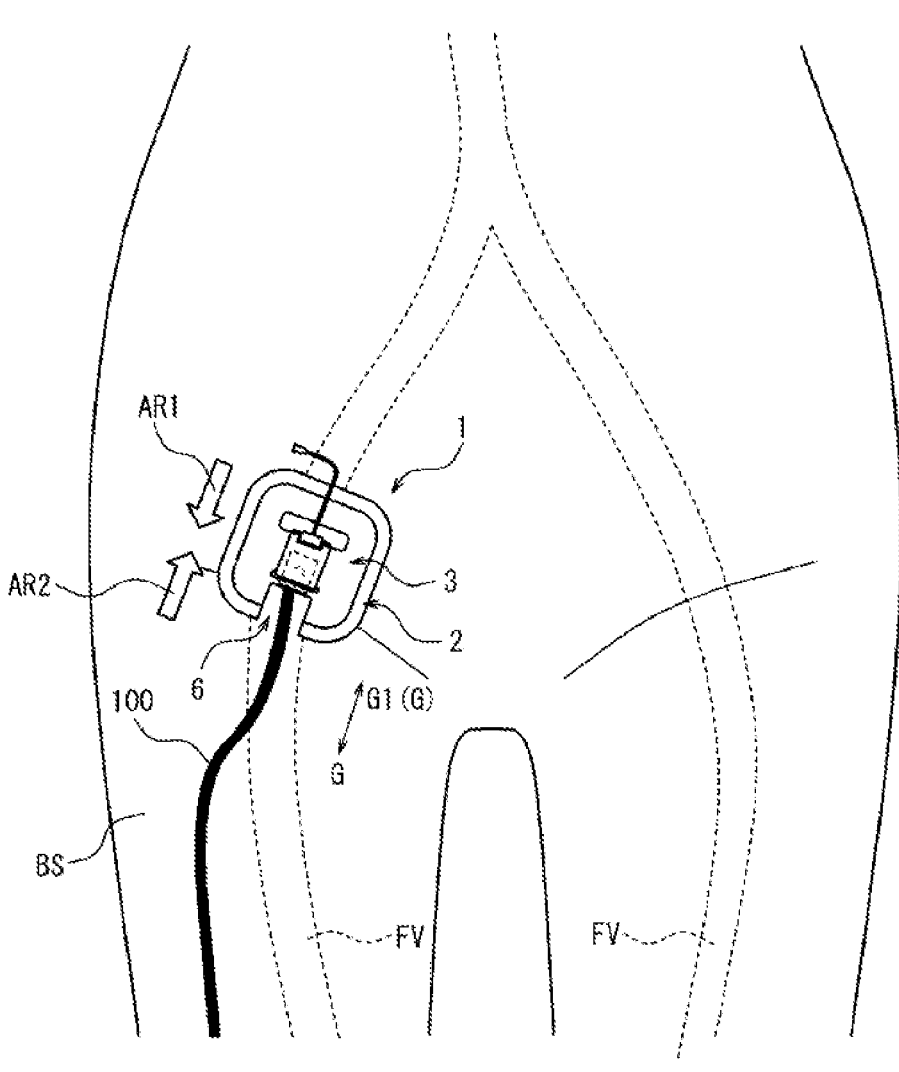
FIG. 14 is a front view of the state shown in FIG. 13 as seen from a biological surface side.

FIG. 14 is a front view of the state shown in FIG. 13 as seen from a biological surface BS side. In other words, FIG. 14 shows a front view of the biological surface BS at a position compressed by the compression device 1. Here, the phrase "front view of the biological surface at a position compressed by the compression device" means a state in which a portion of the biological surface to be compressed by the compression device is seen from a direction perpendicular to the portion before the compressing. FIG. 14 shows a front view of an inguinal region. In the front view shown in FIG. 14, a direction in which the biological surface BS is compressed (see a white arrow "AR1" in FIG. 14) is opposite to an insertion direction G1 (see a white arrow "AR2" in FIG. 14) of the sheath from the biological surface BS toward the vein in an extending direction G of the perforations P. That is, the direction in which the compression device 1 compresses the biological surface BS is opposite to the insertion direction G1 of the sheath in the front view shown in FIG. 14. Accordingly, the perforations P (see FIGS. 12B and 13) are easily narrowed or obstructed without obstructing the vein such as the femoral vein FV.

In other words, as shown in FIG. 13, the extending direction G of the perforations P is inclined with respect to the biological surface BS and is also inclined with respect to the vertical direction (the upward-downward direction in FIG. 13) perpendicular to the biological surface BS. In addition, as shown in FIG. 13, a compression direction of the compression device 1 on the biological surface BS is also inclined with respect to the biological surface BS and also inclined with respect to the vertical direction (the upward-downward direction in FIG. 13) perpendicular to the biological surface BS. Further, as shown in FIG. 13, the extending direction G of the perforations P is inclined to the side opposite to the inclination direction F as the compression direction of the compression device 1 on the biological surface with respect to the vertical direction (the upward-downward direction in FIG. 13). That is, the compression of the compression device 1 on the biological surface is executed such that the compression direction intersects with the extending direction G of the perforations P. Accordingly, the perforations P can be efficiently narrowed or obstructed.

Second Embodiment

Next, a compression device 101 according to a second embodiment will be described. Here, a difference from the above-mentioned compression device 1 (see FIG. 1 or the like) will be mainly described, and a detailed description of features common to both embodiments will not be repeated.

Figure 9A:
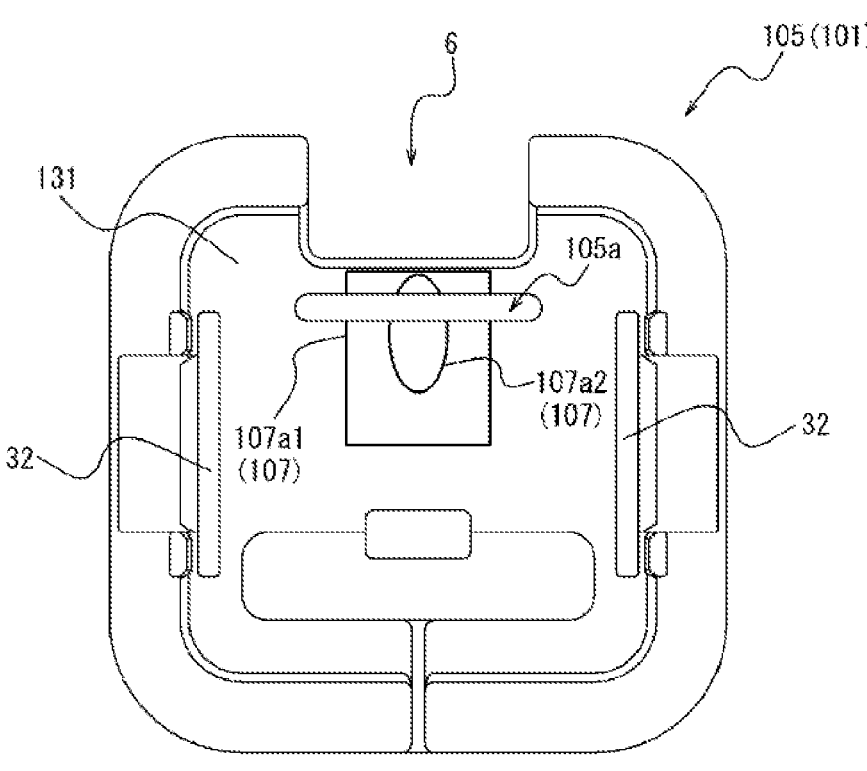
FIG. 9A is a top view of a holding body of a compression device according to a second embodiment of this disclosure.
Figure 9A:
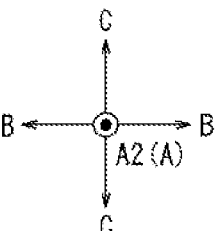

FIG. 9A is a top view of a holding body 105 of the compression device 101 according to the present embodiment. The compression device 101 according to the present embodiment is different from the above-mentioned compression device 1 in a configuration of an identification portion provided in a main body portion of a holding body.

As shown in FIG. 9A, an identification portion 107 is provided on an upper surface of a main body portion 131 of the holding body 105. The identification portion 107 includes two region markers. One region marker is the same frame line marker as the region marker 7*a* according to the first embodiment described above. The other region marker is a frame line marker that further defines a part of a region within the region defined by the one region marker. Hereinafter, for convenience of description, the one region marker that is the same as the region marker 7*a* according to the first embodiment is referred to as a "first region marker 107*a*1". In addition, the other region marker is referred to as a "second region marker 107*a*2".

Since the first region marker 107*a*1 is the same as the region marker 7*a* according to the first embodiment, a detailed description of the first region marker 107*a*1 will not be repeated here.

Within a predetermined region defined by the first region marker 107*a*1 in a plan view seen in the thickness direction A, the second region marker 107*a*2 further defines a part of the predetermined region. The first region marker 107*a*1 means, for example, a region in which a compression force of a first predetermined value or more can be implemented. The second region marker 107*a*2 means, for example, a region in which a compression force of a second predetermined value, which is larger than the first predetermined value, or more can be implemented. Accordingly, by providing the first region marker 107*a*1 and the second region marker 107*a*2, it is possible to switch region markers for aligning the insertion portion 100*a* (see FIG. 8A or the like) of the medical insertion member 100 (see FIG. 8A or the like) according to the outer diameter and the number of the medical insertion member 100 (see FIG. 8A or the like) and a necessary compression force. When the second region marker 107*a*2 is a region in which a large compression force as described above can be obtained, the second region marker 107*a*2 may be, for example, a priority marker that is aligned in preference to the first region marker 107*a*1. That is, only when the insertion portion 100*a* (see FIG. 8A or the like) of the medical insertion member 100 (see FIG. 8A or the like) does not fit within the predetermined region defined by the second region marker 107*a*2, a region outside the second region marker 107*a*2 and inside the first region marker 107*a*1 in the plan view may be used for alignment. If the insertion portion 100*a* (see FIG. 8A or the like) of the medical insertion member 100 (see FIG. 8A or the like) can be disposed only in the region of the second region marker 107*a*2, a fluid amount supplied to the inflatable portion 8 (see FIG. 6 or the like) of the pressing body 4 for stopping bleeding can be reduced. Accordingly, it is possible to prevent the release of the adhesive sheet 2 (see FIG. 6 or the like) from a biological surface.

Both a part of the first region marker 107*a*1 and a part of the second region marker 107*a*2 according to the present embodiment are cut off by a through hole 105*a* of the holding body 105 in the plan view, but this disclosure is not limited to the configuration. The first region marker 107*a*1 and the second region marker 107*a*2 may be provided on only one side with respect to the through hole 105*a* of the holding body 105 in the plan view.

The frame line marker as the first region marker 107*a*1 according to the present embodiment has a rectangular shape, but the shape is not particularly limited. The frame line marker as the first region marker 107*a*1 may have, for example, a circular shape, an oval shape, and a polygonal shape other than a square shape.

The frame line marker as the second region marker 107a2 according to the present embodiment has an oval shape, but the shape is not particularly limited. The frame line marker as the second region marker 107a2 may have, for example, a circular shape and a polygonal shape such as a rectangular shape.

Third Embodiment

Next, a compression device 201 according to a third embodiment will be described. Here, a difference from the compression device 1 (see FIG. 1 or the like) will be mainly described, and a detailed description of the features common to other embodiments will not be repeated.

Figure 9B:
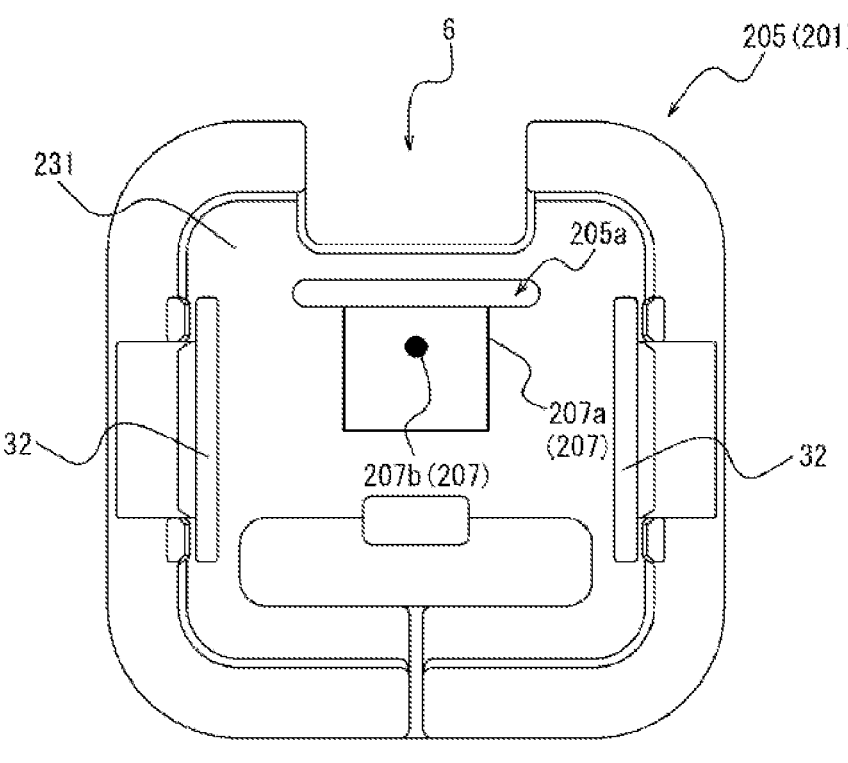
FIG. 9B is a top view of a holding body of a compression device according to a third embodiment of this disclosure.
Figure 9B:
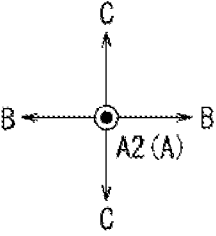

FIG. 9B is a top view of a holding body 205 of the compression device 201 according to the present embodiment. The compression device 201 according to the present embodiment is different from the compression device 1 in a configuration of an identification portion provided in a main body portion of a holding body.

As shown in FIG. 9B, an identification portion 207 includes a region marker 207a and a position marker 207b.

The region marker 207a according to the present embodiment is a concave marker formed by a concave portion formed on an upper surface of a main body portion 231 of the holding body 205. As shown in FIG. 9B, the concave marker as the region marker 207a is bordered in a rectangular shape by an edge portion of the concave portion in a plan view, and defines a predetermined region inside the region marker 207a.

The position marker 207b according to the present embodiment is a point marker disposed in the predetermined region defined by the region marker 207a in the plan view. The point marker as the position marker 207b indicates a predetermined reference position in the plan view. The predetermined reference position can be, for example, a position within the region marker 207a in which a particularly large compression force can be implemented.

The concave marker as the region marker 207a according to the present embodiment has the rectangular shape in the plan view, but the shape is not particularly limited. The concave marker as the region marker 207a may have, for example, a circular shape, an oval shape, and a polygonal shape other than a square shape in the plan view.

The point marker as the position marker 207b according to the present embodiment has a circular shape in the plan view, but the shape is not particularly limited. The point marker as the position marker 207b may have, for example, an oval shape and a polygonal shape such as a rectangular shape in the plan view.

The identification portion 207 according to the present embodiment is provided on only one side with respect to a through hole 205a of the holding body 205 in the plan view, but is not limited to the configuration. The identification portion 207 may be provided on both sides with the through hole 205a interposed therebetween in the plan view.

Fourth Embodiment

Next, a compression device 301 according to a fourth embodiment will be described. Here, a difference from the above-mentioned compression device 1 (see FIG. 1 or the like) will be mainly described, and a detailed description of the features common to other embodiments will not be repeated.

Figure 10:
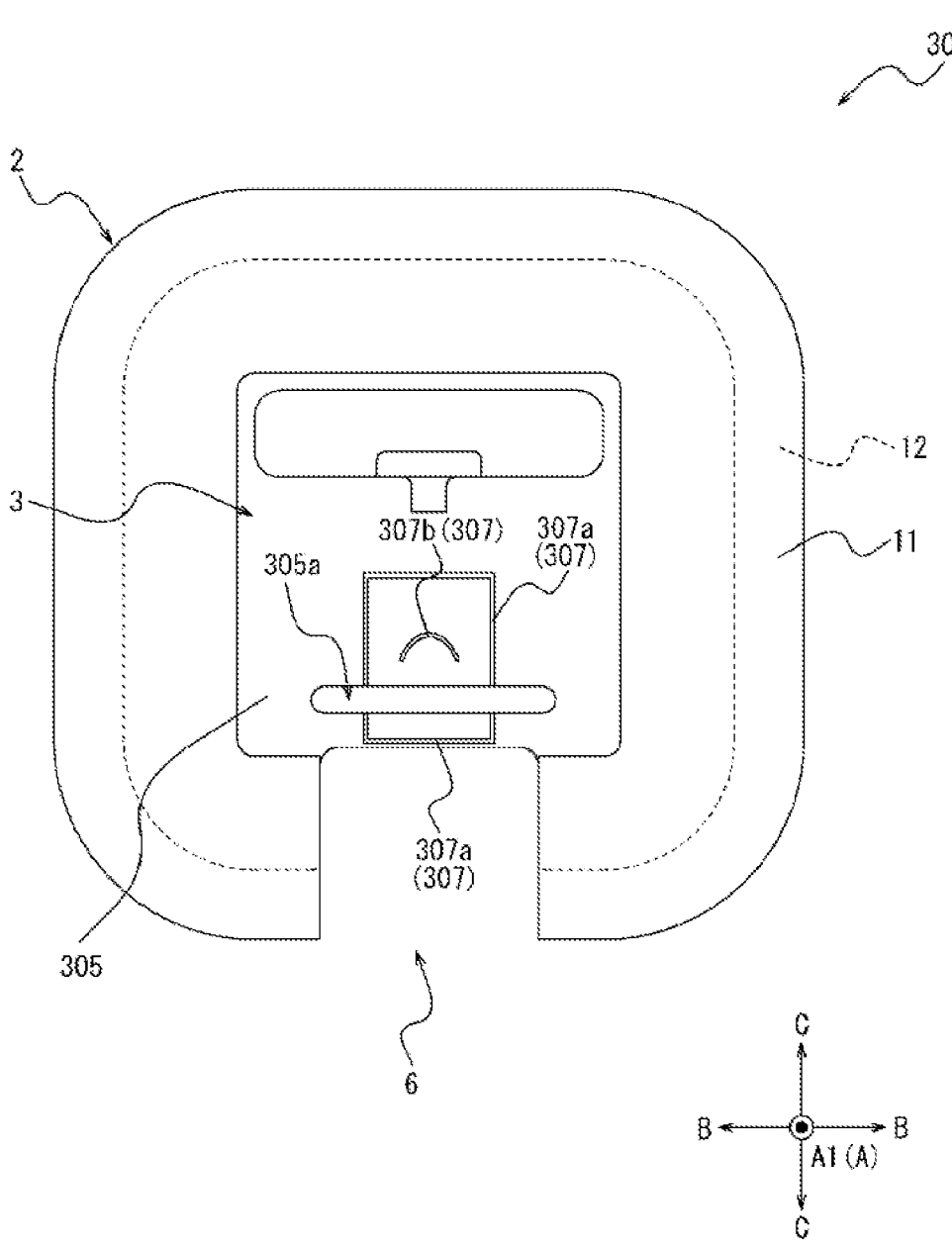
FIG. 10 is a bottom view of a compression device according to a fourth embodiment of this disclosure in a state in which a pressing body is removed.

FIG. 10 is a bottom view of the compression device 301 according to the present embodiment in a state in which the pressing body 4 (see FIG. 1 or the like) is removed. The compression device 301 according to the present embodiment is different from the above-mentioned compression device 1 in a configuration of an identification portion provided in a holding body.

Figure 11:
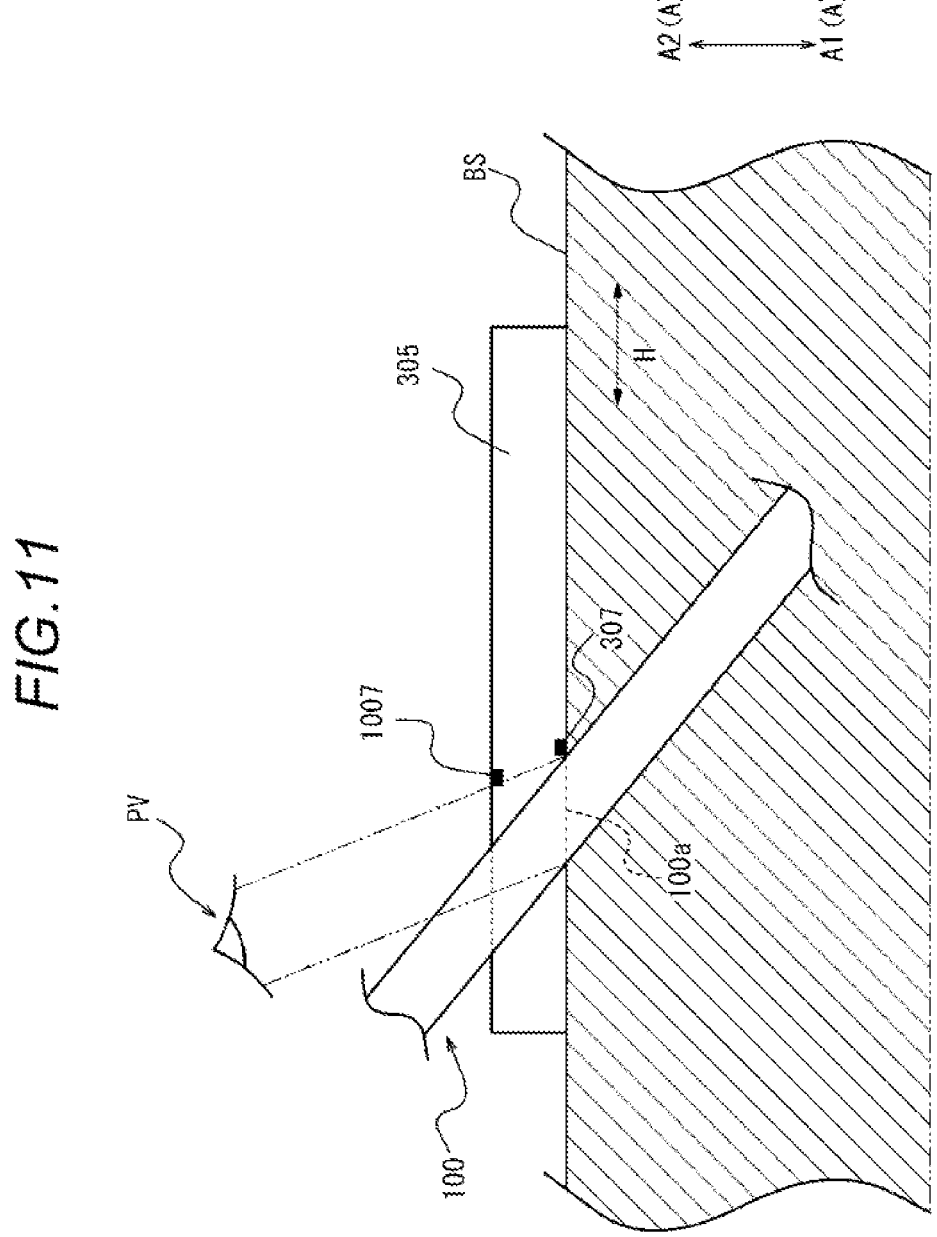
FIG. 11 is a schematic diagram illustrating an effect of an identification portion provided on a lower surface of a holding body in the compression device according to the first embodiment of this disclosure.

An identification portion 307 according to the present embodiment is provided on a lower surface of a holding body 305. FIG. 11 is a schematic diagram illustrating a state in which a part of the outer surface of the insertion portion 100a of the medical insertion member 100, which is located on the same surface as a biological surface, is positioned with respect to the identification portion 307 provided on the lower surface of the holding body 305. In other words, FIG. 11 is a schematic diagram illustrating an effect of the identification portion 307 provided on the lower surface of the holding body 305. For convenience of description, FIG. 11 shows an identification portion 1007 provided on an upper surface of the holding body 305 for comparison. As shown in FIG. 11, by providing the identification portion 307 on the lower surface of the holding body 305, it is possible to prevent occurrence of positional variation caused by a thickness of the holding body 305 in the thickness direction A, as compared with the configuration in which the identification portion 1007 is provided on the upper surface of the holding body 305. That is, when the identification portion 1007 is provided on the upper surface of the holding body 305, the identification portion 1007 is separated from the biological surface on a lower surface side of the holding body 305 by at least the thickness of the holding body 305. Therefore, when the identification portion 1007 is aligned at a predetermined position on the biological surface at an erroneous viewpoint (for example, a viewpoint PV shown in FIG. 11) deviated from a plan view, the identification portion 1007 and the predetermined position on the biological surface (a part of the outer surface of the insertion portion 100a in FIG. 11) may be positionally deviated in an in-plane direction H of the biological surface. On the other hand, according to the present embodiment, since the identification portion 307 is provided on the lower surface of the holding body 305, the above-mentioned positional deviation due to a difference in viewpoint is less likely to occur. That is, by providing the identification portion 307 on the lower surface of the holding body 305, the compression device 301 can be more easily attached to an appropriate position on the biological surface.

As shown in FIG. 10, the identification portion 307 includes a region marker 307a and a position marker 307b.

The region marker 307a according to the present embodiment is a frame line marker that defines a predetermined region by a rectangular groove portion formed on the lower surface of the holding body 305. In addition, the position marker 307b according to the present embodiment is a line segment marker formed by a groove portion extending in an arc shape formed on the lower surface of the holding body 305.

A part of the region marker 307a according to the present embodiment is cut off by a through hole 305a of the holding body 305 in the plan view, but is not limited to the configuration. The region marker 307a may be provided on only one side with respect to the through hole 305a of the holding body 305 in the plan view.

The frame line marker as the region marker 307a according to the present embodiment has a rectangular shape in the plan view, but the shape is not particularly limited. The frame line marker as the region marker 307a may have, for example, a circular shape, an oval shape, and a polygonal shape other than a square shape in the plan view.

The line segment marker as the position marker 307*b* according to the present embodiment extends in the arc shape in the plan view, but the shape is not particularly limited. The line segment marker as the position marker 307*b* may extend in, for example, a linear shape or a V shape in the plan view.

The compression device and the method for adhering the compression device according to this disclosure are not limited to the specific configurations and the methods shown in the first embodiment to the fourth embodiment described above, and various modifications and changes may be made without departing from the description of the claims. In addition, a compression device formed by combining the configurations of the portions of the compression device shown in the first embodiment to the fourth embodiment also belongs to the technical scope of this disclosure.

The detailed description above describes embodiments of a compression device, a method for adhering a compression device and a compression method representing examples of the new compression device, compression device adhering method and compression method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST 1, 101, 201, 301 compression device
2 adhesive sheet
3 compression member
4 pressing body
5, 105, 205, 305 holding body
5*a*, 105*a*, 205*a*, 305*a* through hole
5*b* locking protrusion
6 receiving portion
7, 107, 207, 307 identification portion
7*a*, 207*a*, 307*a* region marker
7*b*, 207*b*, 307*b* position marker
8 inflatable portion
8*a* accommodation space
8*b*, 8*c* balloon portion
9 extending portion
9*a* hinge portion
9*b* locking hole
11 adhesion surface
12 attachment surface
28 tube
29 connection portion
30 syringe
31, 131, 231 main body portion
32 a pair of gripping plate portions
100 medical insertion member
100*a* insertion portion
107*a*1 first region marker
107*a*2 second region marker
1007 identification portion
A thickness direction
A1 downward direction
A2 upward direction
B width direction C arrangement direction
F inclination direction
G extending direction of perforation
G1 insertion direction of sheath
H in-plane direction of biological surface
BS biological surface
CT connective tissue
FV femoral vein
P perforation
PV viewpoint
X1 first portion of adhesive sheet
X2 second portion of adhesive sheet

What is claimed is:

1. A compression device to be adhered to a biological surface of a living body to apply compression to a puncture site penetrating the biological surface of the living body, the compression device comprising:

an adhesive sheet that includes an adhesion surface configured to face towards and be adhered to the biological surface, the adhesion surface being a lower surface of the adhesive sheet, the adhesive sheet also including an upper surface spaced from the lower surface of the adhesive sheet in a thickness direction of the adhesive sheet, the adhesive surface being configured to surround an open central area of the adhesive sheet as seen in a plan view of the compression device, the open central area of the adhesive sheet extending in the thickness direction of the adhesive sheet so that the open central area of the adhesive sheet is open at both the upper and lower surfaces of the adhesive sheet, the adhesive sheet possessing an outer periphery;

a holding body fixed to the upper surface of the adhesive sheet and spanning across the open central area of the adhesive sheet, the holding body including an outer edge;

a pressing body mounted on the holding body so that the pressing body is held by the holding body at a position in the open central area of the adhesive sheet, the pressing body being configured to expand in the thickness direction to apply the compression to the puncture site penetrating the biological surface of the living body when the adhesive sheet is adhered to the biological surface;

the adhesive sheet including a receiving portion constituted by a cut-out portion of the adhesive sheet that is cut-out from the outer periphery of the adhesive sheet toward the open central area of the adhesive sheet, the receiving portion being located radially outwardly of the outer edge of the holding body as seen in the plan view of the compression device and being configured to receive an elongated medical insertion member located in the puncture site penetrating the biological surface of the living body;

the holding body including an identification portion that is visually identifiable in the plan view and that identifies a location for positioning the compression device relative to the elongated medical insertion member when the compression device is adhered to the biological surface of the living body, the identification portion being located adjacent to and inwardly of the receiving portion as seen in the plan view of the compression device;

the identification portion including a region marker and a position marker;

the region marker being constituted by a visually identifiable line that outlines a predetermined region in the plan view so that when the adhesive sheet is adhered to the biological surface, the elongated medical insertion portion of the medical insertion member is located within the predetermined region and is surrounded by the visually identifiable line; and the position marker being an arc shape line in the plan view, the arc shape line being open along a side facing towards the receiving portion, the arc shape line being located within the predetermined region as seen in plan view and identifying a predetermined reference position within the predetermined region outlined by the region marker.

2. The compression device according to claim 1, wherein the predetermined region outlined by the region marker is configured so that when the adhesive sheet is adhered to the biological surface a portion of the medical insertion member, which is located at the biological surface, is entirely located within the predetermined region.

3. The compression device according to claim 2, wherein the adhesive sheet is C-shaped so that the C-shaped adhesive sheet encircles the open central area and terminates at two ends that face each other and are spaced apart from each other, with a space between the two ends, the space between the two ends of the C-shaped adhesive sheet constituting the cut-out portion of the adhesive sheet.

4. The compression device according to claim 3, wherein the side of the arc shape line that is open faces toward the space.

5. The compression device according to claim 1, wherein the adhesive sheet is an annular-shaped adhesive sheet that encircles the open central area, the annular-shaped adhesive sheet terminating at two ends that face each other and are spaced apart from each other, with a space between the two ends, the space between the two ends of the annular-shaped adhesive sheet constituting the cut-out portion of the adhesive sheet, the visually identifiable line constituting the region marker is a U-shaped line that is open along a side facing towards the space.

6. The compression device according to claim 1, wherein the pressing body is comprised of an inflatable portion having an interior configured to receive a fluid to inflate and expand the inflatable portion, the pressing body also comprising an extending portion fixed to the holding body to fix a position of the inflatable portion, the extending portion overlying, as seen in the plan view of the compression device, a part of the holding portion at which the identification portion is located.

7. The compression device according to claim 1, wherein the pressing body includes an inflatable portion having an interior configured to receive a fluid to inflate and expand the inflatable portion, the visually identifiable line that outlines the predetermined region and that constitutes the region marker overlapping the inflatable portion of the pressing body in the plan view of the compression device.

8. A compression device comprising:

an adhesive sheet having an adhesion surface configured to be adhered to a biological surface, the adhesive sheet possessing a thickness that extends in a thickness direction of the adhesive sheet;

a compression member that is fixed to the adhesive sheet and that is configured to compress the biological surface;

the compression member including a pressing body configured to press the biological surface by extending in the thickness direction of the adhesive sheet, and a holding body that is fixed to the adhesive sheet on a side opposite to the adhesion surface and that holds the pressing body so that the pressing body is extendable in the thickness direction, the holding body including an outer edge;

a receiving portion configured to receive a medical insertion member, the receiving portion being provided outside the outer edge of the holding body as seen in a plan view in the thickness direction, the receiving portion being a region in which the adhesive sheet is not disposed or a region defined by a concave portion in an outer edge of the adhesive sheet;

the holding body including, at a position adjacent to the receiving portion, an identification portion configured to be visually identified in the plan view seen in the thickness direction;

the identification portion including a region marker and a position marker;

the region marker being constituted by a visually identifiable line that outlines a predetermined region in the plan view so that when the adhesive sheet is adhered to the biological surface, the elongated medical insertion portion of the medical insertion member is located within the predetermined region and is surrounded by the visually identifiable line; and the position marker being an arc shape line in the plan view, the arc shape line being open along a side facing towards the receiving portion, the arc shape line being located within the predetermined region as seen in plan view and identifying a predetermined reference position within the predetermined region outlined by the region marker.

9. The compression device according to claim 8, wherein the pressing body includes an inflatable portion configured to be disposed between the biological surface and the holding body in a state in which the adhesion surface of the adhesive sheet is adhered to the biological surface, the pressing body being inflatable in the thickness direction by supplying a fluid to the inflatable portion, and at least a part of the visually identifiable line constituting the region marker overlaps with the inflatable portion of the pressing body in the plan view seen in the thickness direction.

10. The compression device according to claim 8, wherein the adhesive sheet is an annular-shaped adhesive sheet that encircles an open central area, the annular-shaped adhesive sheet terminating at two ends that face each other and are spaced apart from each other, with a space between the two ends, the space between the two ends of the annular-shaped adhesive sheet constituting the receiving portion of the adhesive sheet.

11. The compression device according to claim 10, wherein the region marker is a frame line marker that surrounds a portion having translucency in the thickness direction.

12. The compression device according to claim 10, wherein the holding body includes a portion having translucency in the thickness direction in an adjacent periphery outside the region marker in the plan view seen in the thickness direction.

13. The compression device according to claim 10, wherein the visually identifiable line constituting the region marker is a U-shaped line that is open along a side facing towards the space.

14. The compression device according to claim 13, wherein the visually identifiable line constituting the region marker is a U-shaped line that is open along a side facing in a same direction as the side of the arc shape line that is open.

15. A method for adhering a compression device on a biological surface, the compression device including:

an adhesive sheet having an adhesion surface configured to be adhered to the biological surface, the adhesive sheet possessing a thickness that extends in a thickness direction of the adhesive sheet;

a compression member that is fixed to the adhesive sheet and that is configured to compress the biological surface;

the compression member including:

a pressing body configured to press the biological surface by extending in the thickness direction of the adhesive sheet; and a holding body that is fixed to the adhesive sheet on a side opposite to the adhesion surface and that holds the pressing body so that the pressing body is extendable in the thickness direction, the holding body including an outer edge;

a receiving portion configured to receive a medical insertion member, the receiving portion being provided outside the outer edge of the holding body as seen in a plan view in the thickness direction, the receiving portion being a region in which the adhesive sheet is not disposed or a region defined by a concave portion in an outer edge of the adhesive sheet;

the holding body including, at a position adjacent to the receiving portion, an identification portion configured to be visually identified in the plan view seen in the thickness direction, the identification portion including a region marker and a position marker;

the region marker being constituted by a visually identifiable line that outlines a predetermined region in the plan view so that when the adhesive sheet is adhered to the biological surface, the elongated medical insertion portion of the medical insertion member is located within the predetermined region and is surrounded by the visually identifiable line; and the position marker being an arc shape line in the plan view, the arc shape line being open along a side facing towards the receiving portion, the arc shape line being located within the predetermined region as seen in plan view and identifying a predetermined reference position within the predetermined region outlined by the region marker the method comprising adhering the adhesive sheet to the biological surface while the medical insertion member extends into a living body from the biological surface, a portion of the medical insertion member being exposed to outside the biological surface, the adhering of the adhesive sheet to the biological surface including adhering the adhesive sheet to the biological surface so that the portion of the medical insertion member that is exposed to outside the biological surface is received in the receiving portion, and the adhering of the adhesive sheet to the biological surface including adhering the adhesive sheet to the biological surface while an insertion portion of the medical insertion member, which is located on a surface that is the same as the biological surface, is aligned with the identification portion.

16. The adhering method according to claim 15, wherein the adhering of the adhesive sheet to the biological surface including adhering the adhesive sheet to the biological surface while an entirety of the insertion portion of the medical insertion member, which is located on the surface that is the same as the biological surface, is aligned within the region marker.

17. The adhering method according to claim 16, wherein the adhering of the adhesive sheet to the biological surface including adhering the adhesive sheet to the biological surface while a part of the insertion portion is aligned with the position marker.

18. The adhering method according to claim 15, wherein the adhering of the adhesive sheet to the biological surface includes adhering the adhesive sheet to the biological surface so that the insertion portion of the medical insertion member, which is located on the surface that is the same as the biological surface, is entirely located within the predetermined region and is surrounded by the visually identifiable line.

19. The adhering method according to claim 18, wherein the adhering of the adhesive sheet to the biological surface including adhering the adhesive sheet to the biological surface so that the insertion portion of the medical insertion member, which is located on the surface that is the same as the biological surface, is entirely located within the predetermined reference position and is surrounded by the arc shape line.

20. The compression device according to claim 19, wherein the visually identifiable line constituting the region marker is a U-shaped line that is open along a side facing the receiving portion.

* * * * *